United States Patent [19]

Heilman et al.

[11] Patent Number: 5,383,840
[45] Date of Patent: Jan. 24, 1995

[54] BIOCOMPATIBLE VENTRICULAR ASSIST AND ARRHYTHMIA CONTROL DEVICE INCLUDING CARDIAC COMPRESSION BAND-STAY-PAD ASSEMBLY

[75] Inventors: Marlin S. Heilman, Sarver; Steve A. Kolenik, Leechburg; Christopher D. Capone, Pittsburgh; Carl M. Parisi, Kittanning; Edward K. Prem, Allison Park; Vernon L. Speicher, Leechburg, all of Pa.

[73] Assignee: Vascor, Inc., Pittsburgh, Pa.

[21] Appl. No.: 920,732

[22] Filed: Jul. 28, 1992

[51] Int. Cl.⁶ .............................................. A61H 31/00
[52] U.S. Cl. ....................................... 600/17; 601/153
[58] Field of Search ................ 600/16, 17; 128/54, 128/60, 64

[56] References Cited

U.S. PATENT DOCUMENTS

| | | | |
|---|---|---|---|
| 2,238,967 | 4/1941 | Brown | 128/63 |
| 2,814,727 | 11/1957 | Gund et al. | 250/49.5 |
| 3,233,607 | 2/1966 | Bolie | 128/64 |
| 3,279,464 | 10/1966 | Kline | 128/64 |
| 3,371,662 | 3/1968 | Heid et al. | 128/24.5 |
| 3,455,298 | 7/1969 | Anstadt | 128/64 |
| 3,513,836 | 5/1970 | Sausse | 128/64 |
| 3,587,567 | 6/1971 | Schiff | 128/24.5 |
| 3,668,708 | 6/1972 | Tindal | 623/3 |
| 3,915,158 | 10/1975 | Simjian | 128/56 |
| 4,048,990 | 9/1977 | Goetz | 128/64 |
| 4,092,742 | 6/1978 | Kantrowitz et al. | 623/3 |
| 4,167,046 | 9/1979 | Portner et al. | 623/3 |
| 4,192,293 | 3/1980 | Asrican | 600/16 |
| 4,291,707 | 9/1981 | Heilman et al. | 607/129 |
| 4,304,225 | 12/1981 | Freeman | 128/60 |
| 4,448,190 | 5/1984 | Freeman | 128/60 |
| 4,506,658 | 3/1985 | Casile | 600/16 |
| 4,536,893 | 8/1985 | Parravicini | 623/3 |
| 4,541,417 | 9/1985 | Kirkorian | 600/17 |
| 4,583,523 | 4/1986 | Kleinke et al. | 600/16 |
| 4,621,617 | 11/1986 | Sharma | 600/16 |
| 4,690,134 | 9/1987 | Snyders | 128/64 |
| 4,731,076 | 3/1988 | Noon et al. | 623/3 |
| 4,925,443 | 5/1990 | Heilman et al. | 600/16 |
| 4,957,477 | 9/1990 | Lundbäck | 600/16 |
| 5,081,986 | 1/1992 | Cho | 128/62 |
| 5,098,369 | 3/1992 | Heilman et al. | 600/16 |
| 5,131,905 | 7/1992 | Grooters | 600/16 |
| 5,150,706 | 9/1992 | Cox et al. | 607/113 |

FOREIGN PATENT DOCUMENTS 2060174  4/1981  United Kingdom .

*Primary Examiner*—William E. Kamm
*Attorney, Agent, or Firm*—Keck, Mahin & Cate

[57] ABSTRACT

A ventricular assist device for a heart includes a compression band-stay-pad assembly for encircling substantially the entire heart perimeter and comprising an elongated band member or chain disposed in a sealed protective structure filled with a lubricating medium. The band member may be fixed at one end and wound upon, or unwound from, a rotatable spool by a drive motor through a speed reducer. Force-transmitting support or stay assemblies are disposed in the protective structure between the band member and a resilient pad assembly for encircling the heart and promoting heart tissue ingrowth therein. The force-transmitting stay assemblies are biased circumferentially, and thus radially outward, by compression return springs disposed therebetween. The resilient pad assembly includes a corrugated surface provided with vertical coil springs, which help prevent damage to heart tissue and facilitate return of the pad assembly to an initial condition, embedded defibrillator electrodes and relatively soft portions to prevent damage to coronary arteries. The device may be constructed so that it can be surgically removed, except for a sealing film and an ingrown pad of the resilient pad assembly, which remain in situ on the heart. A net structure suspended below the device supports the apical portion of the heart.

46 Claims, 15 Drawing Sheets

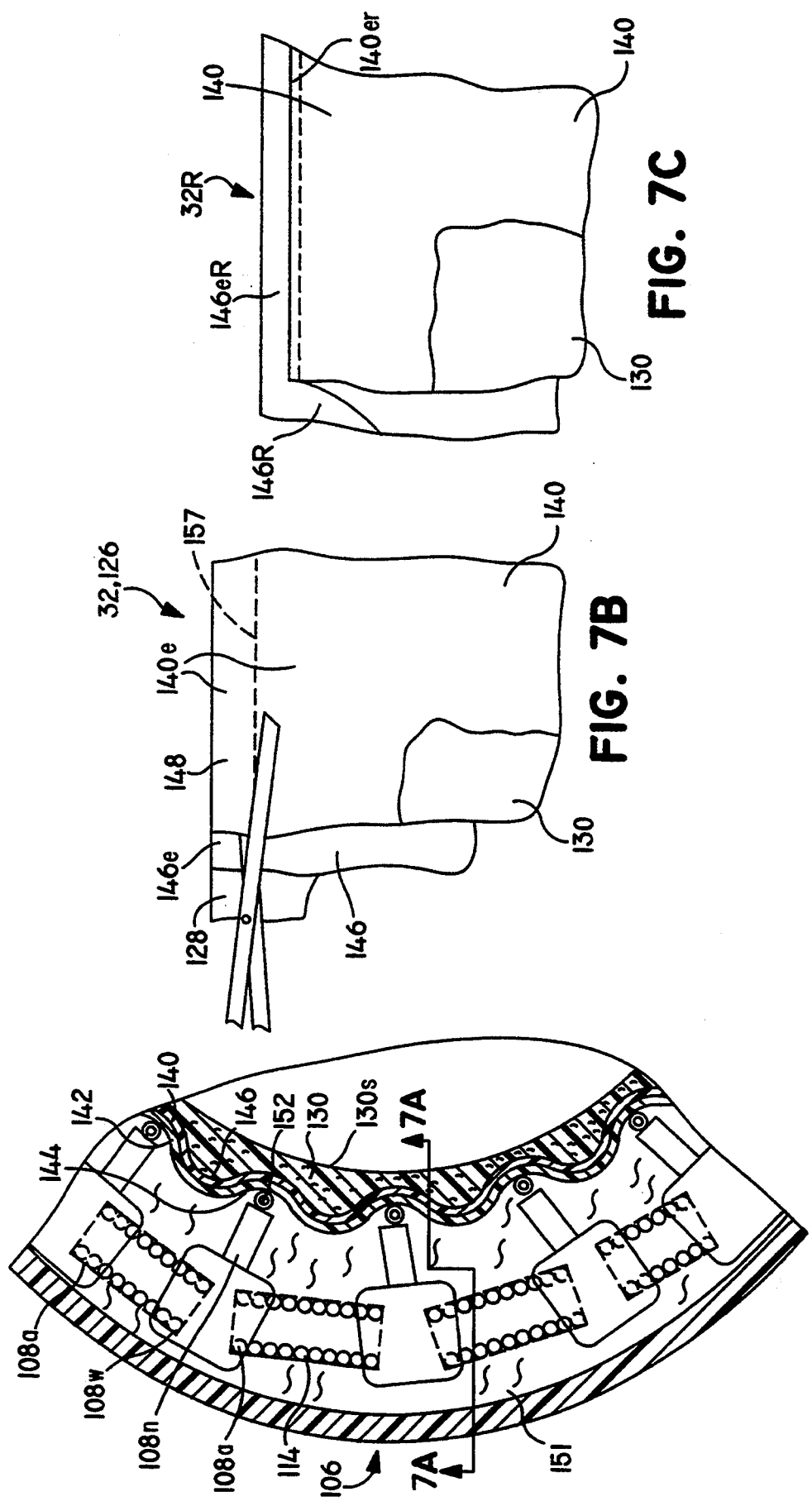

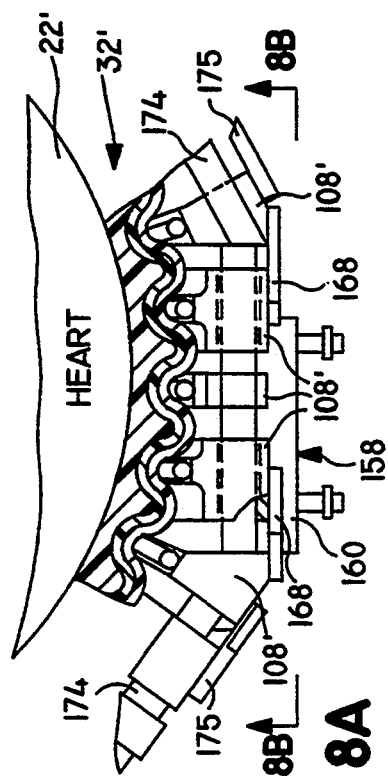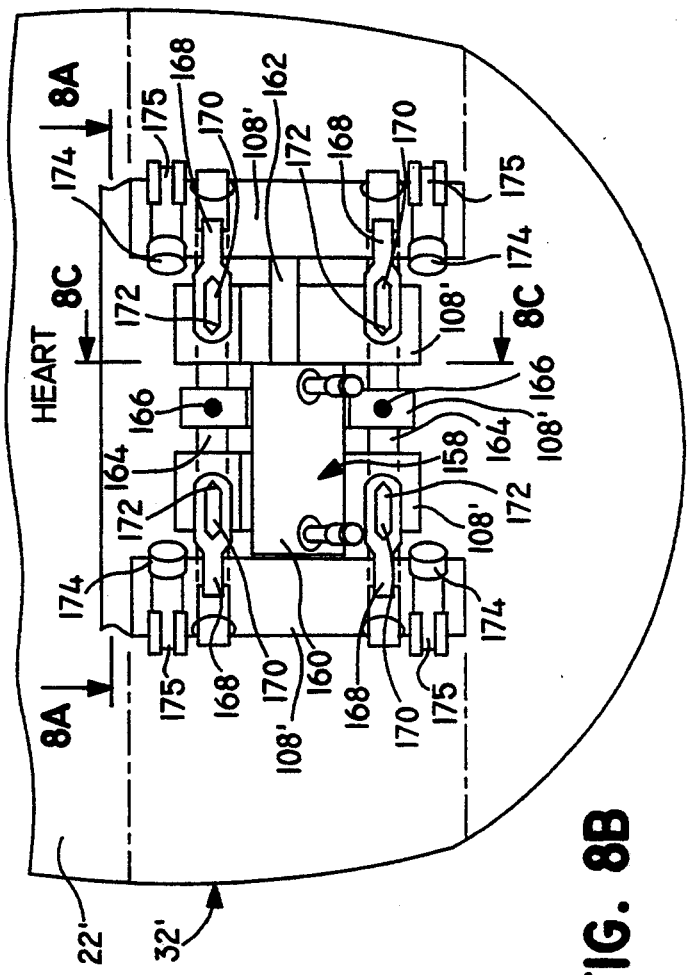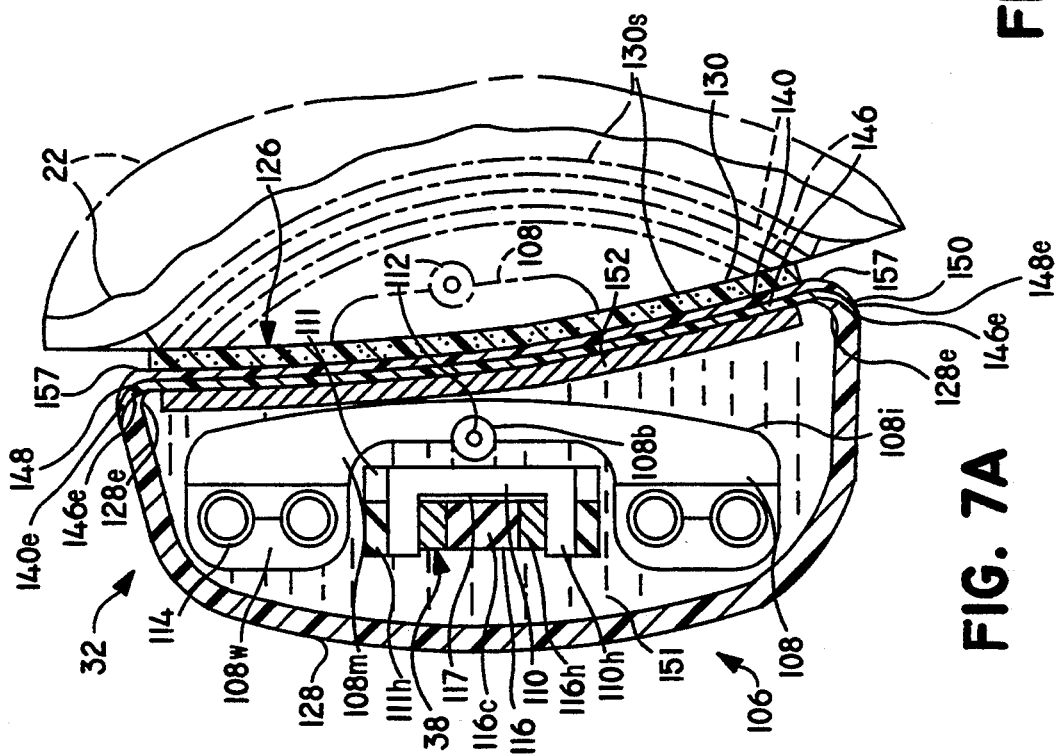

BIOCOMPATIBLE VENTRICULAR ASSIST AND ARRHYTHMIA CONTROL DEVICE INCLUDING CARDIAC COMPRESSION BAND-STAY-PAD ASSEMBLY

BACKGROUND OF THE INVENTION

1. Field of the Invention

This invention relates to a biocompatible ventricular assist and arrhythmia control device, and more particularly to a biocompatible ventricular assist and arrhythmia control device comprising a cardiac ventricular compression band-stay-pad assembly, for compressing and assisting in the contraction and expansion of one or both heart ventricles, without damaging the ventricle.

2. Description of the Prior Art

U.S. Pat. No. 4,925,443, issued May 15, 1990, to Marlin S. Heilman and Steve A. Kolenik, entitled "Biocompatible Ventricular Assist and Arrhythmia Control Device", discloses an implantable ventricular assist device which includes (1) one or more movable compression assemblies for engaging a ventricle of the heart; (2) an operating mechanism for cyclically actuating the movable compression assemblies and thereby alternately ejecting blood from the ventricle and permitting the ventricle to refill; (3) a sensing means to detect adequacy of ventricular stroke volume and/or pressure; (4) a control mechanism to assure adequate ventricular stroke volume by regulating the compressive force of the compression assemblies, and also to control pacemaker, cardioverter/defibrillator, and recorder subsystems; and (5) an electrical power source.

In that patent, each compression assembly includes a contoured pressure plate and a soft contact pad mounted on the interior plate surface for suturing and/or gluing the compression assembly to the ventricle. To minimize mechanical stress on the myocardial surface, including the coronary arteries, the contact pad consists of an elastomer, such as silicone rubber, or a thermoplastic material (Shore A durometer range 30-50). To avoid edge stress, the thickness of each contact pad is progressively reduced toward its periphery. To further reduce stresses on the myocardium, bearings and axles are used to mount the pressure plates on the compression assembly's driving arm; if the contracting heart produces a torquing force, the joint will permit the pressure plate, within specified limits, to follow the natural movement of the heart.

Similarly, to help prevent the edges of the compression assembly pressure plates from creating pressure points which might cause possible damage to the heart, a related continuation-in-part U.S. patent application Ser. No. 07/019,701, filed May 14, 1990, in the names of Marlin S. Heilman, et al., entitled "Biocompatible Ventricular Assist and Arrhythmia Control Device Including Cardiac Compression Pad and Compression Pad Assembly", now U.S. Pat. No. 5,098,369, discloses replacing the contact pad of each compression assembly with a gel-filled contact pad of special construction which compresses the heart ventricle more uniformly without damaging the ventricle.

Other previous attempts to provide ventricular assistance have ranged from artificial hearts (e.g., the Jarvik-7), to devices which directly pump the blood via an artificial pathway inserted through the ventricular wall, to devices which exert pressure on the outside of the heart. Most frequently, these latter pressure-exerting devices involve some form of flexible bladder within a support structure such that expansion of the bladder presses on the ventricle and facilitates expulsion of blood. See, for example, U.S. Pat. Nos. 3,233,607 to Bolie; 3,279,464 to Kline; 3,587,567 to Schiff; 3,371,662 to Heid et al.; 4,048,990 to Goetz; 4,192,293 to Asrican; 3,455,298 to Anstadt; 4,690,134 to Snyder; 4,731,076 to Noon et al.; and 4,957,477 to Lundback. Another structurally related device (U.S. Pat. No. 4,506,658 to Casile) envisions a truncated conical structure of sac-lined rigid panels separated by contractible and expandable sections, and another device (U.S. Pat. No. 4,621,617 to Sharma), which is electromagnetically controlled, comprises a pair of hinged compression members. Further, U.S. Pat. No. 4,536,893 to Parravicini envisions using two segmented sacs, selectively fed by a pumping fluid to compress the right and left ventricles separately.

In general, bladder systems usually have various shortcomings. These include the possibility of catastrophic bladder fluid leakage (as a result of the fluid pressures involved), a propensity for damaging the heart surface due to poor fixation and/or rubbing of the bladder against the heart's surface, and the unnatural convex form presented to the heart's surface during systolic bladder expansion.

Another type of cardiac assist system is designed to compress all or part of the heart by alternately tightening and releasing a compression band. For example, one proposed system for body organs (U.S. Pat. No. 4,304,225 to Freeman), such as the heart, involves a flexible strap which is fixed to a contoured plastic block and passes across the back of the heart. In response to electrical pulses, a motor assembly alternately reels in and releases the flexible strap, thereby tending to flatten and force fluid from the heart.

The above-mentioned Freeman patent also discloses the use of a tubular compression sleeve which substantially encircles the heart and which comprises a series of interconnected expandable elliptical chambers. In use, a liquid solution is pumped into the sleeve from a supply chamber, causing the elliptical chambers to expand radially inward to compress the heart in its systolic phase. The solution then is released from the sleeve back to a supply chamber, permitting the heart to expand in its diastolic phase.

U.S. Pat. No. 4,583,523 to Kleinke and Freeman illustrates a heart assist mechanism which compresses the aorta, rather than a ventricle, and it compresses during the diastolic phase of cardiac contraction instead of the systolic phase. Other known prior art of interest includes U.S. Pat. Nos. 3,668,708 to Tindal, 4,167,046 to Portner, 4,092,742 to Kantrowitz et al. and 4,291,707 to Heilman, German Patent Document No. DE-A-2,557,475, British Patent Document No. GB-A-2,060,174 and U.S.S.R. Patent Document No. SU-1572646-A1.

SUMMARY OF THE INVENTION

In general, this invention relates to an implantable ventricular assist device which may include (1) one or more motor mechanisms for converting electrical and/or hydraulic energy to a mechanical motion for constricting the perimeter about the heart; (2) movable support or "stay" assemblies for transmitting the motor-induced mechanical motion into a compressive action on the heart's surface; and (3) a pad or interface assembly between the movable stay assemblies and the surface of the heart, the pad assembly serving a number of purposes including the minimization of various mechanical stresses that might otherwise damage the heart and/or coronary arteries.

A presently preferred embodiment of the invention includes a band-stay-pad assembly positionable about at least one heart ventricle and comprising an elongated band member or chain that activates stay assemblies housed in a fluid lubricant-filled chamber. Included is a mechanism for fixing one end of the band member essentially against movement. Additionally, there is a rotatable support for winding at least a portion of the band member thereon relative to the lubricant-filled chamber housing the stay assemblies, as a result of the band member having an opposite end connected to the rotatable support, and a reversible drive mechanism for rotating the rotatable support in one direction to wind up the portion of the band member and thereby compress the heart ventricle during a systolic phase thereof, and rotating the rotatable support in a reverse direction to unwind the portion of the band member from the rotatable support, to release the heart ventricle during a diastolic phase thereof.

More specifically, the drive mechanism may include a drive motor and a planetary gear-type speed reducer connected to the rotatable support. The band member, together with the supports or stays, and stay links, as well as longitudinally extending and circumferentially arranged return springs, is encased in a compressible and expandable protective structure, which defines the above-mentioned lubricant-filled chamber and which may comprise a partially corrugated and inner foam-surfaced pad or interface assembly that contacts the heart's surface and is continuous, for fluid sealing purposes, with a flexible membrane defining an outside surface of the structure. The stay assemblies comprise: (1) the stay links that are slotted for receiving portions of the movable band and which are interleaved with band portions so as to provide an aligned path for the band; (2) the stays, which may pivot and are connected to inner sides of respective ones of the stay links, typically by means of rocking joints; (3) a series of the circumferentially extending springs that return the band-stay-pad assembly to its beginning (end-diastolic) position; and (4) longitudinally and vertically extending force-transmitting springs that are supported on the pad assembly and respective ones of the pivoting stays, and have opposite end portions which flex outward as the band-stay-pad assembly compresses into the heart's surface. The return springs bias the compression band-stay-pad assembly circumferentially, and thus also radially outward, with the pad assembly being preferably secured to the heart's surface by suturing and/or ingrowth, so that outward expansion of the heart, or diastolic filling, is assisted by the springs.

In other embodiments, the motor-driven chain is replaced by a plurality of other types of motor mechanisms provided between selected ones of the stays to assist in contraction and expansion of the heart. The band-stay-pad assembly also may be formed initially with an adjustable portion by which the assembly can be fitted around a patient's heart in "customized" close-fitting relationship, and multiple compression bands or chains movable in opposite directions may be utilized.

The present invention, as above described, overcomes a number of obstacles and complications inherent in state-of-the-art devices and as disclosed in previously issued patents. For example, U.S. Pat. Nos. 4,925,443 and 5,098,369 (Heilman et al.) disclose devices which have discrete compression plates that, although effective for pumping purposes, could under certain circumstances pinch the surface of the heart between the edges of the compression plates. The present invention represents an improvement over these devices because it produces a more complete enclosure of the heart's surface, obviating the risk of pinching.

In other known prior art which utilizes a compression band extending about only a portion of the heart, the action of the band is to flatten the heart and either slide on the heart's surface or splint, i.e., prevent the surface from undergoing a natural shortening or contraction action. Flattening the heart produces an unnatural bending of the heart's muscle, and the sliding action of the band on the heart's surface is abrasive. The band-stay-pad invention described herein also is advantageous over these type devices in that it eliminates hard surfaces or edges being in contact with the heart so as to avoid pinching, while also avoiding flattening or shearing of the heart tissue.

Further, with the subject invention, the bottom or apical portion of the heart is supported by a collapsible net structure having limited expansion ability. Should an infarct (death) of the heart's muscle occur from a blockage of a coronary artery, the band-stay-pad assembly with its attached net then will provide support and thus avoid or limit any aneurysmal ballooning or rupture of the heart that otherwise might occur.

Many patients suffer from a form of heart failure caused by fibrous replacement of heart muscle tissue resulting in muscle stiffening. The present invention also is advantageous in this regard in that it has the capability to both increase heart filling by a slight return spring-induced stretch during diastole, and increase the depth of contraction during systole, and therefore heart emptying, thus overcoming the effects of the abnormal heart muscle stiffness.

From the standpoint of space requirements in the patient's body, the ventricular assist device of the present invention also is advantageous in that it has the form of a flexible envelope that fits in the natural cleavage plane about the heart, with the envelope's attached motor drive fitting, for example, in the natural cleavage plane between the diaphragm and the lower lobe surface of the left lung. Because of these desirable fit properties and the relatively small size of the device, surgical complications also are expected to be less than with other known assist devices.

The pad assembly, which defines an inner lining of the invention, comprises an inner foam pad having a sealing film on an outer corrugated surface, and has a number of other unique features. For example, it is formed in a fashion and will be acted upon by the stay assemblies so as to shrink in the circumferential dimension much the same as the heart surface does naturally. This action, together with the porosity of its foam surface, will promote tissue ingrowth and adhesion of the pad to the heart's surface, thus avoiding shear stress at the pad-heart surface interface. The foam pad also can be made to possess a degree of hardness, Shore A 30–50, that is similar to that of heart muscle, thus further avoiding unnecessary stress.

By embedding metallic cables constructed of numerous small diameter wires in the corrugated porous foam pad, it also is possible to effectively create large surface area defibrillating electrodes since the foam porosity will allow electric current to flow and the small wire diameters will resist flex-fracturing. The corrugated sealing film on the stay assembly side of the pad assembly also is sufficiently thin (less than 20 mils) to avoid fatigue fracture from millions of compression cycles and may be constructed of multiple layers secured together along their upper and lower edges, with only the innermost layer bonded to the foam pad, and only the outermost layer adjacent to the stay assemblies sealed to edges of the outside surface membrane for retaining the fluid lubricant. Then, should it be necessary to surgically replace the band-stay portion of the device, it also is an option to leave in place the innermost film and the foam pad, which has become connected to the heart by tissue ingrowth. A replacement device then would have its own fluid-sealing layer of corrugated film that would mate with and be suitably attached to the in situ film layer secured to the foam pad. The compression band-stay-pad assembly and a housing of the drive mechanism may be filled with a biocompatible medium, such as mineral oil, which functions as the above-mentioned fluid lubricant and also prevents body fluids from seeping into the device.

BRIEF DESCRIPTION OF DRAWINGS

FIG. 6 is an enlarged cross-sectional view of a portion of FIG. 5;

FIG. 7A is a cross-sectional view taken essentially along the line 7A—7A in FIG. 6;

FIGS. 7B and 7C are schematic views illustrating removal and securing steps in a device replacement procedure;

FIG. 8A is a partial top view of a second embodiment of the invention, partially in cross-section;

FIG. 8B is an enlarged, elevational view as seen essentially along the line 8B—8B in FIG. 8A;

DETAILED DESCRIPTION

Figure 1:
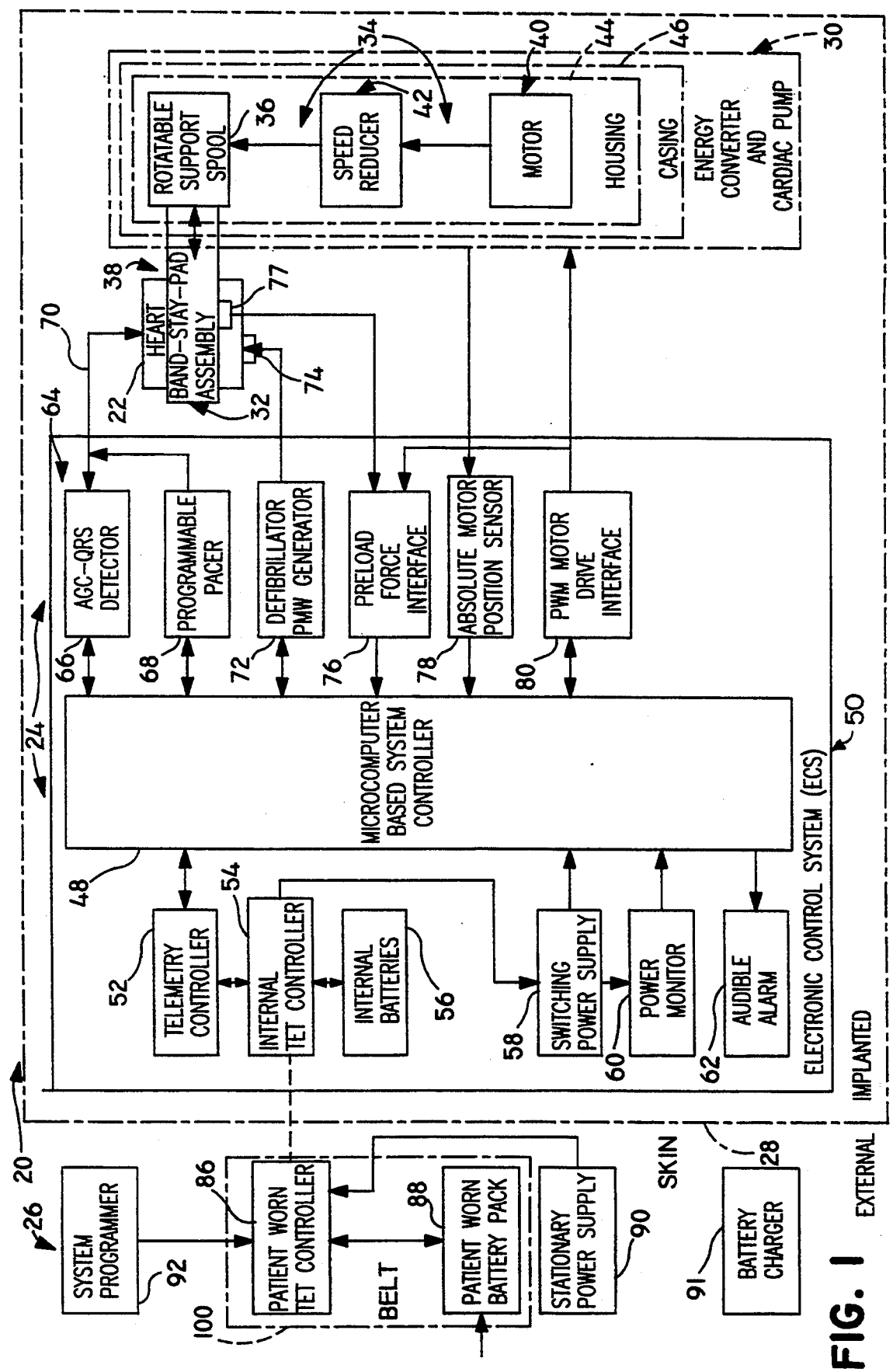
FIG. 1 is a schematic block diagram of a ventricular assist device in accordance with a first embodiment of the invention;.
Figure 2:
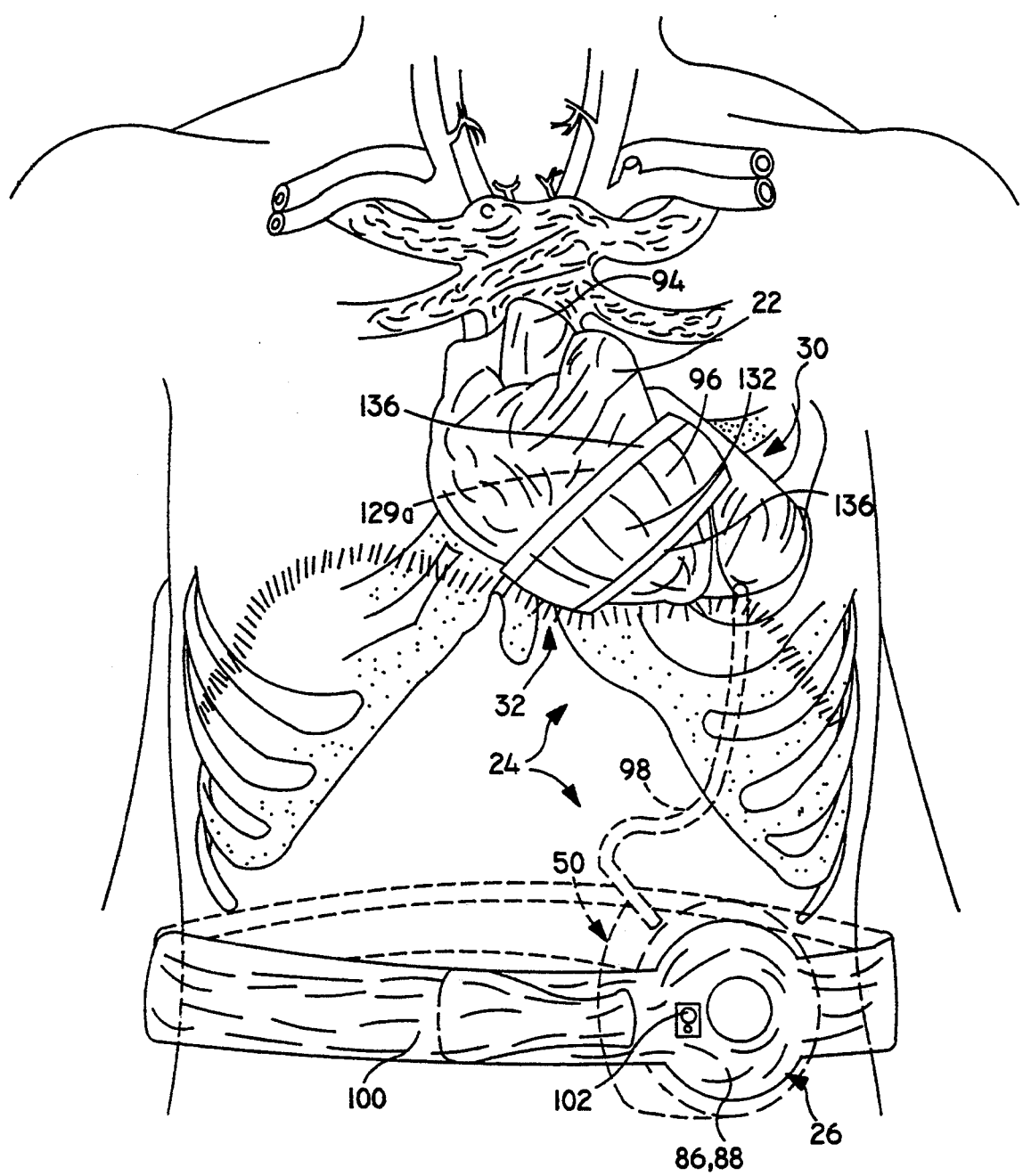
FIG. 2 is a schematic general front elevational view of the upper portion of a patient's body showing the ventricular assist device implanted on the heart, with the heart shown in its diastolic phase.

FIG. 1 discloses a block diagram of a biocompatible ventricular assist and arrhythmia control device 20 in accordance with a first embodiment of the invention, hereinafter referred to as the ventricular assist device, it being understood that numerous other variations of the invention are, of course, possible. As disclosed in FIG. 1, the ventricular assist device 20, which operates in synchronism with a heart 22, comprises an implantable subsystem 24 and a subsystem 26 external to, and without penetrating, a patient user's skin 28. The implantable subsystem 24 includes a direct cardiac energy converter and cardiac pumping mechanism 30 which includes a heart compression band-stay-pad assembly 32, and a drive mechanism 34 comprising a rotatable support spool 36 for winding a band member or chain 38 of the band-stay-pad assembly thereon, and unwinding the band member therefrom, a drive motor 40, a speed reducer 42 connected between the drive motor and the rotatable support spool, and a housing 44 in which the rotatable support spool, drive motor and speed reducer are mounted. The drive motor 40, through the speed reducer 42 and the rotatable support spool 36, mechanically initiates radially inward ventricle-assist motion of the compression band-stay-pad assembly 32 when the heart 22 begins to contract, limits and controls the degree of mechanical compression, and terminates the degree of compression so that the compression band-stay-pad assembly may return to its original radially outward position as the heart refills. The housing 44 is at least partially encapsulated in a casing 46 of a suitable biocompatible material, such as titanium, SILASTIC® silicone elastomer (Dow Corning Corp., Midland, Mich.) or DURAFLEX™ polyurethane (Vascor, Inc., Pittsburgh, Pa.). The energy converter and cardiac pumping mechanism 30 also includes sensors (not shown) which provide input to a microcomputer based system controller 48, within an electronic control system module 50 implantable in the patient's body remote from the energy converter and cardiac pumping mechanism, as illustrated in FIG. 2.

The electronic control system module 50, in addition to the microcomputer based system controller 48, includes a telemetry controller 52, an internal transcutaneous energy transmission (TET) controller 54, internal batteries 56, a switching power supply 58, a power monitor 60 and an audible alarm 62. The electronic control system module 50 further includes a cardiac pacer system 64 comprising an automatic gain controlled (AGC) R-wave or QRS complex (electrocardiogram waveform just prior to systolic contraction) detector circuit 66, and a programmable pacer 68 connected to an electrocardiogram (ECG)/pacer lead 70 positionable upon the patient's heart 22 in a known manner. A cardioversion/defibrillation pulse generator 72 also is connected to one or more defibrillation electrodes 74 also mountable upon the patient's heart as subsequently discussed with reference to FIGS. 4A and 5. The controller 48 may be connected to the energy converter-and-cardiac pumping mechanism 30 by a system including a preload force interface 76 connected to a dedicated force transducer 77 of the compression band-stay-pad assembly 32, an absolute motor position sensor 78, and a pulse width modulated (PWM) motor drive interface 80.

Power is transmitted from the external subsystem 26 to the electronic control system 50 by a patient-worn TET controller 86 and the internal TET controller 54. External power is provided by either a patient-worn battery pack 88 or a stationary power supply 90. When the battery pack 88 is expended, it may be recharged with a battery charger 91. In addition, a system programmer 92 may be selectively connected to the patient-worn TET controller 86 for programming and interrogation.

The programmer 92 may comprise a programmed personal computer system of a known type, the details of which are not shown, which includes a small printer/plotter, a transtelephonic data transmission device and an AC power supply, with battery backup. A series of menus, displayed on a computer screen, prompt the operator to select the desired system control parameters at a keyboard. All selected programming options are automatically logged at the printer and stored on a 3.5 inch floppy disk. Additionally, when commanded, the programmer 92 will display, record and plot two selected real-time signals (ECG, refractory pulse, motor torque, compression band position, or band velocity) for a selectable time period, such as 2.5 or 5.0 seconds.

FIG. 2 shows the ventricular assist device 20, essentially as represented by the block diagram of FIG. 1, with the internal subsystem 30 implanted in an upper portion of a patient's body for assisting the heart 22 in the pumping of blood from the heart, through its major artery (aorta) 94, and to the arterial system. In the disclosed arrangement the energy converter and cardiac pumping mechanism 30 is located adjacent a heart left ventricle 96, between the patient's diaphragm or inside the chest wall of the patient, and the lower lobe surface of the left lung, with the compression band-stay-pad assembly 32 fitting in a natural cleavage plane about the heart, and encircling the heart. The electronic control system module 50 is implanted adjacent the waist of the patient user and is connected to the energy converter and cardiac pump mechanism 30 via a communications and power supply link 98. The external patient-worn TET controller 86 and battery pack 88 are disposed in a belt 100 which may be worn around the patient user's waist inside or externally of the patient user's clothing and which may be removably secured by a quick-releasable material of a known type at opposite ends of the belt. The TET controller 86 and battery pack 88 preferably are distributed in the belt 100 around a substantial portion of the belt for the patient's comfort. The abovementioned programming of the implanted electronic control system 50 can be accomplished from the programming device 92 (FIG. 1), by connecting the programming device to the patient-worn TET controller 86 via a cord and plug assembly (not shown) insertable into a plug receptacle 102 (FIG. 2) on the belt 100. The recharging of the patient-worn battery pack 88 may be accomplished by removing the battery pack or the belt 100 for a recharging operation by the battery charger 91, and replacing the battery pack with a fully charged battery pack, or replacing the belt with a belt having a fully charged battery pack, to provide continuous, tether-free operation.

Figure 4B:
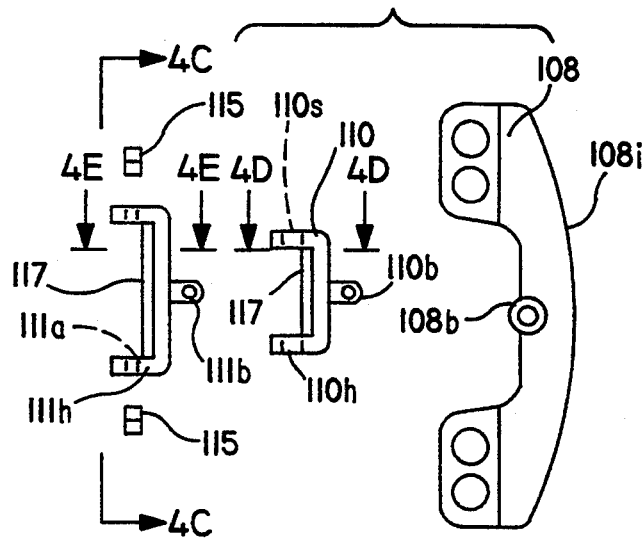
FIG. 4B is an exploded view of a plurality of parts of the ventricular assist device.
Figure 4C:
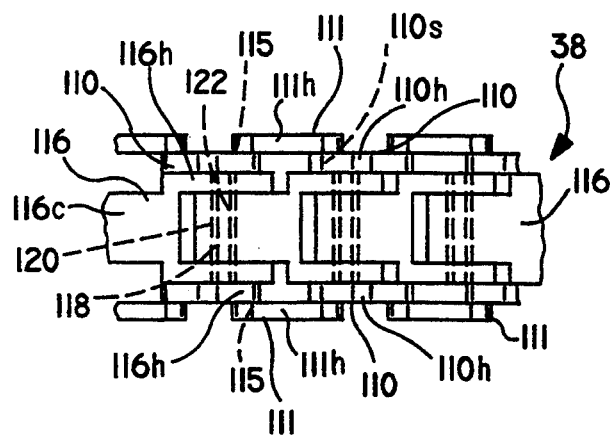
FIG. 4C is a schematic elevational view of certain parts as shown in FIG. 4B, as seen in the direction of the arrows 4C—4C.
Figure 4A:
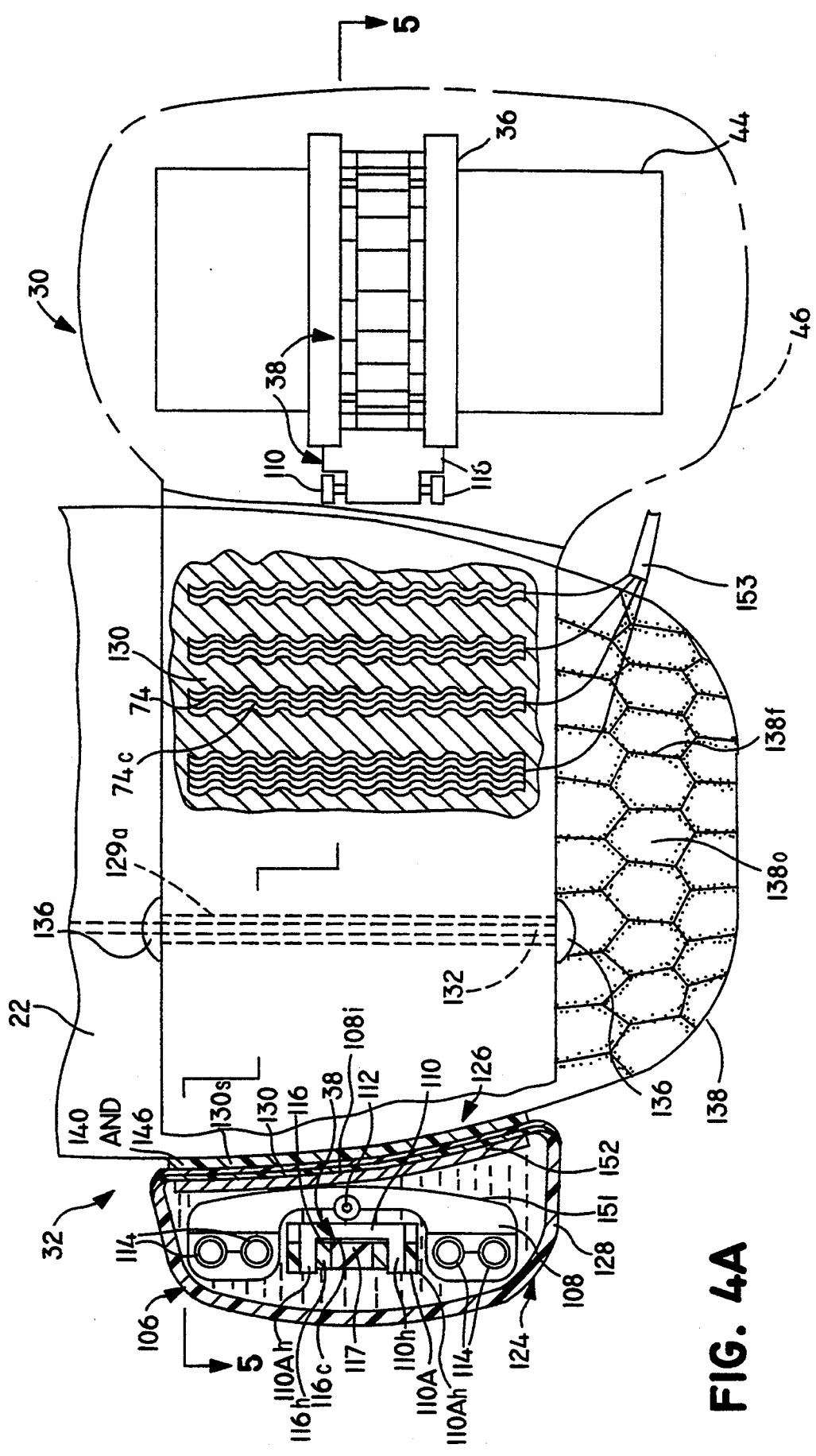
FIG. 4A is an enlarged elevational view, partially in cross section, illustrating in greater detail the ventricular assist device attached to the patient's heart.
Figure 5:
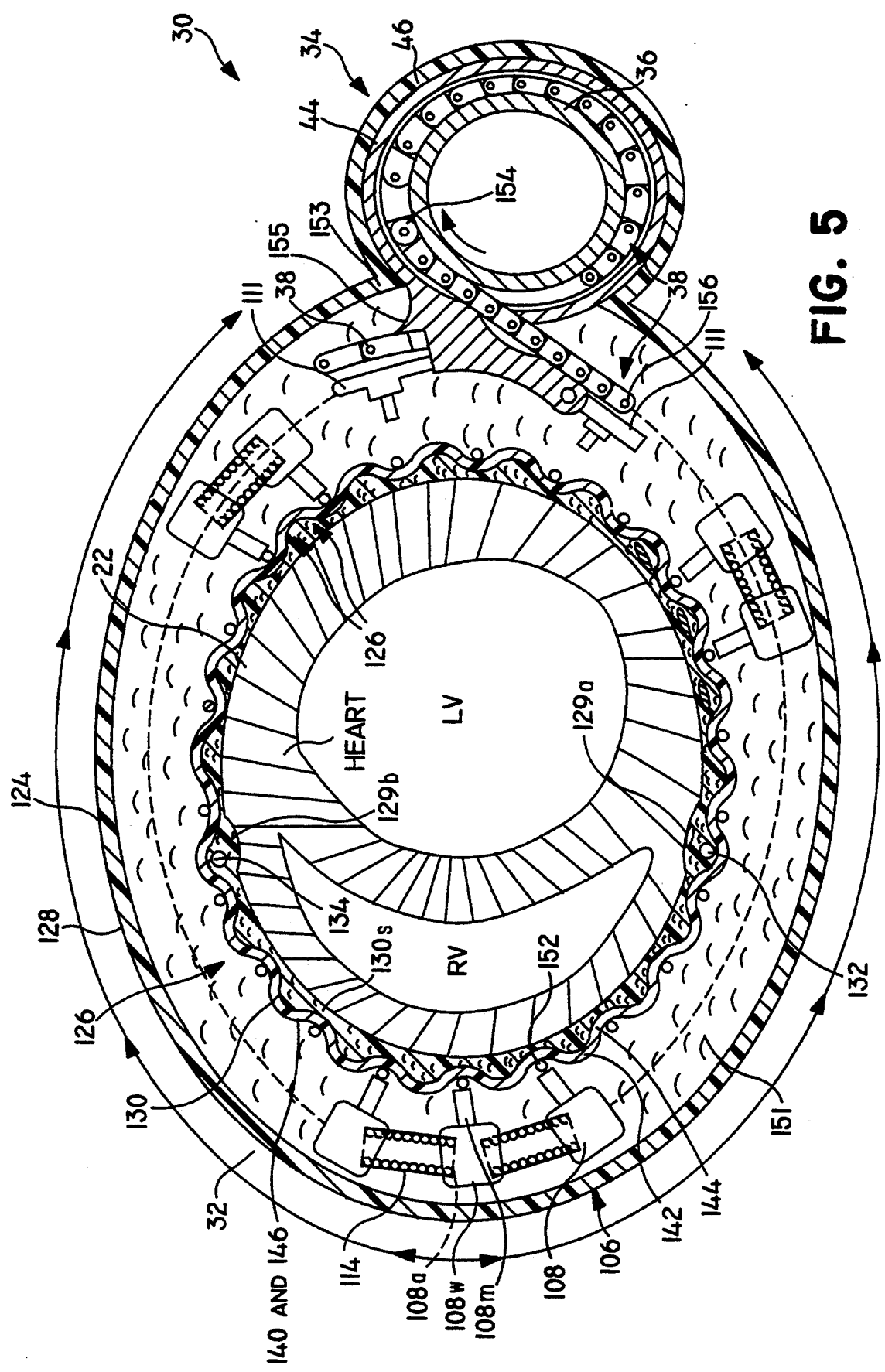
FIG. 5 is a schematic cross-sectional view, with certain parts omitted, taken essentially along the line 5—5 in FIG. 4A.

Referring to FIGS. 4A, B and C, and FIG. 5, the compression band-stay-pad assembly 32 comprises the elongated band member or chain 38, which may be in the form of a pivoted link chain of a suitable material, such as a composite plastic compound like carbon reinforced polyphenylene sulfide (PPS), or carbon reinforced polyether ketone. For example, the carbon reinforced polyphenylene sulfide (PPS) may be an injection molded plastic composite including polyphenylene sulfide, TEFLON ®, carbon fibers and silicone, available from LNP Engineering Plastics of Exton, Pa. The chain material also may be a metal, e.g., a cobalt based alloy such as that available from SPS Technologies, Inc., of Jenkingtown, Pa. under the trademark MP35N, or that available from Eligloy Limited Partnership of Elgin, Ill., under the trademark ELIGLOY, a stainless steel (316L), titanium, or a composite of PPS and metal. The elongated band member or chain 38 also is encased in a protective structure 106 of the band-stay-pad assembly 32 for preventing damage to the heart 22 and/or surrounding tissue.

The compression band-stay-pad assembly 32 further comprises a plurality of C-shaped rigid support or "stay" members 108, preferably supported centrally for rocking movement on respective alternating channel-shaped stay link members 110 and 111, by bearing portions 108b, 110b and 111b (FIG. 4B), respectively, and associated hinge or pivot pins 112. The stays 108 have enlarged relatively wide end portions 108w (best shown in FIGS. 5 and 6) each provided with a pair of apertures 108a for receiving respective ends of circumferentially extending, compression-return coil springs 114, and also have relatively narrow force-transmitting portions 108n. Alternatively, the return springs 114 may be mounted on enlarged portions of the stay links 110 and 111. The stays 108, and the stay links 110 and 111, may be formed of a biocompatible metal, such as commercially pure titanium or a titanium alloy (e.g., Ti-6AL-4V), or the abovementioned injection molded plastic composite used for the chain 38.

Figure 4D:
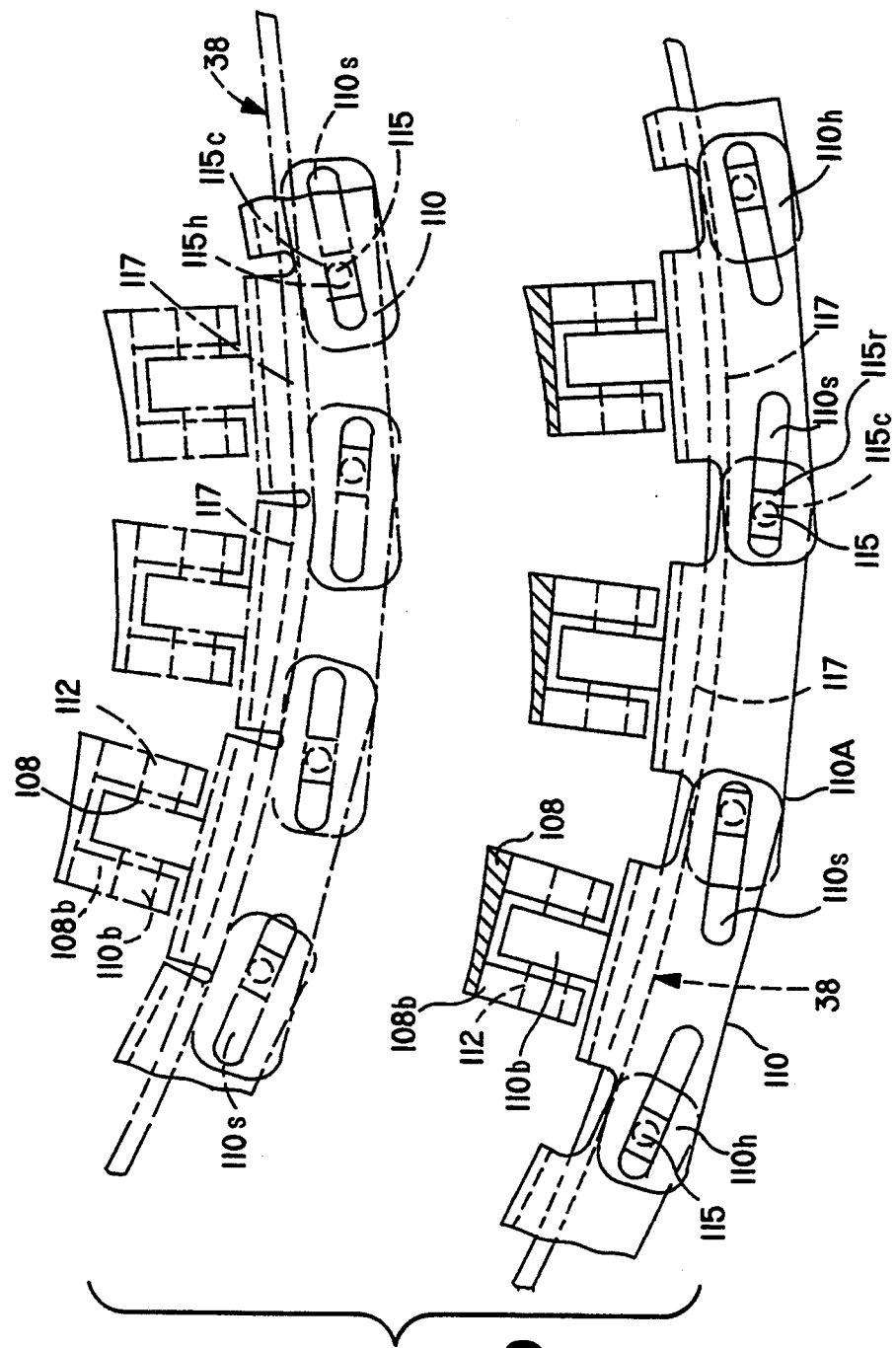
FIG. 4D is a cross-sectional view of one of the parts shown in FIG. 4C, taken along the line 4D—4D.
Figure 4E:
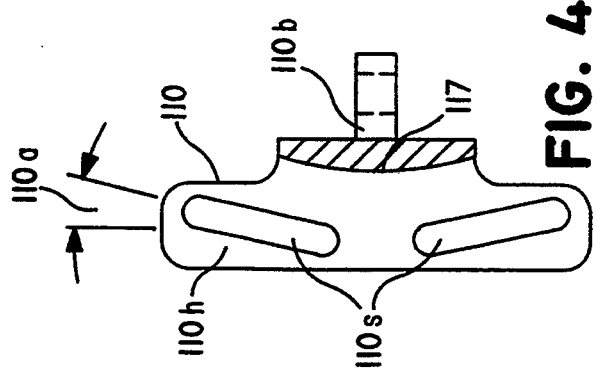
FIG. 4E is a cross-sectional view of another of the parts shown in FIG. 4C, taken along the line 4E—4E.

The stay links 110 and 111 provide a mechanism by which the stay members 108 and the link chain 38 are supported in adjacent relationship. For this purpose, vertically spaced, horizontal legs 110h (FIGS. 4B, C and D) of each stay link 110 are formed with elongated slots 110s (best shown in FIG. 4D) disposed at an angle 110a on the order of 6⅛° to a longitudinal axis of the legs. Each of the stay links 111 includes horizontal legs 111h having opposite end portions which receive adjacent end portions of the stay links 110 therebetween.

Figure 4F:
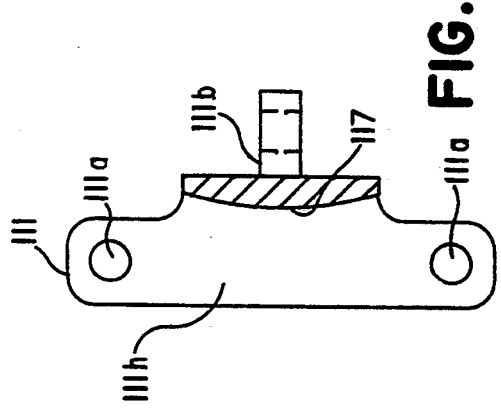
FIG. 4F is a cross-sectional view of the parts shown in FIGS. 4D and 4E in assembled relationship.

The legs 111h include apertures 111a by which these legs are connected to the legs 110h of the stay links 110 by suitable pins 115 having cylindrical portions 115c (FIG. 4F) fixedly mounted in the apertures and also having rectangular portions 115r disposed for sliding movement in the slots 110s for alignment control. In operation, with reference to FIG. 4F, the stay links 110 and 111 move between solid line positions (diastole) and broken line positions (systole).

Figure 12A:
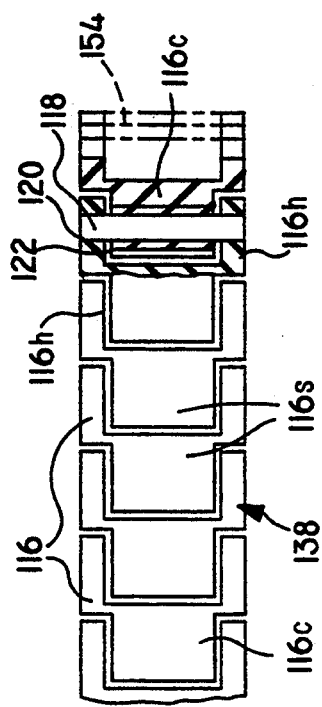
FIG. 12A is a partial elevational view, partially in cross-section, of an end portion of an operating chain for a ventricular assist device in accordance with the invention shown in FIGS. 1–7.
Figure 12B:
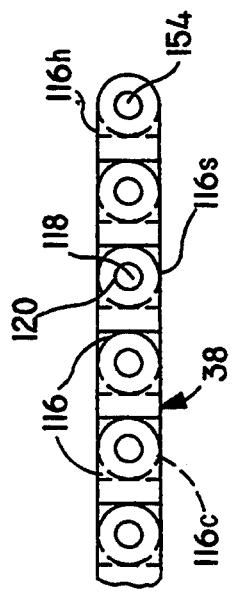
FIG. 12B is a plan view of the end portion of the operating chain shown in FIG. 12A.

Referring to FIG. 4C, the legs 110h and 111h of the stay links 110 and 111 are disposed on upper and lower sides of the chain 38, which comprises chain members 116 having horizontal legs 116h and central portions 116c received between respective ones of the horizontal legs, with the chain riding on arcuate bearing surfaces 117 (FIG. 4B) of the stay links. As is also shown in FIGS. 12A and 12B, the chain members 116 are pivotally interconnected by pins 118 having opposite ends fixed in apertures 120 in the horizontal legs 116h, and intermediate portions journaled in suitable bearings 122 in the central portions 116c. The chain members 116 may be formed of a suitable plastic composite or a metal, as noted previously. Other chain configurations also may be used, such as miniaturized bicycle-type chains, but to minimize wear at the chain-engaging surfaces 117 of the stay links 110 and 111, the stay link surfaces should be plastic if the surfaces of the chain 38 are metal or metal if the chain surfaces are plastic.

With further reference to FIGS. 4A and 5, the structure comprising the stays 108, the stay links 110 and 111, and the associated portion of the chain 38, is encased by a sheath assembly 124 comprising an inner pad or interface assembly 126 and an outer membrane 128. To prevent excessive pressure on main heart coronary arteries 129a and 129b (see FIGS. 2, 3, 4A and 5) during the systole phase of the heart 22, a pressure pad 130 of the inner pad assembly 126 preferably is formed in two essentially semi-circular segments having opposed ends separated by first and second tubular portions 132 and 134, respectively, as shown in FIG. 5, which are formed of a relatively softer foam material, and which are suitably sealed closed at their upper and lower ends by plug portions 136 (see FIG. 4A). When the band-stay-pad assembly 32 is positioned on the heart 22, the first tubular portion 132 is located over the main coronary artery 129a (left anterior descending) and the second tubular portion 134 is located on the opposite side of the heart 22 over the right coronary main artery 129b. Thus, in compression of the heart 22 by the band-stay-pad assembly 32 during the heart's systole phase, the relatively soft tubular portions 132 and 134 cooperate to reduce the relative pressure applied on the main coronary arteries 129a and 129b.

As is shown in FIG. 4A, the bottom or apical portion of the heart 22 is supported by a collapsible, but essentially non-expandable net structure 138 having its upper periphery bonded to the underside of the sheath assembly 124 around its perimeter, with the net structure being movable radially inward and outward therewith. Thus, should an infarct (death) of the heart's muscle occur from a blockage of a coronary artery, the net 138 will provide support and avoid or limit any aneurysmal ballooning or rupture of the heart 22 that may otherwise occur. By way of example, the net structure 138 may be formed from a polyester fiber bundle 138f having a diameter in a range on the order of 0.6 to 2.6 mm, with elongated net openings 138o having short and long dimensions on the order of 3 mm and 8 mm, respectively.

The pressure pad 130 is formed of a relatively soft material and has a smooth inner surface 130s which is engageable with the heart 22 without causing damage to the heart tissue. The pad material also is of a type which can be sutured to the heart 22 and also preferably is relatively porous in nature to enhance tissue ingrowth and bonding of the pad to the heart, so that radial expansion of the band-stay-pad assembly 32 assists in expansion of the heart during its diastole phase. For example, a suitable material for this purpose is polyurethane foam, at least the inner heart-contacting surface 130s of which has been treated with an anti-microbial agent, such as cephalosporin.

As is shown in FIG. 6, an outwardly facing surface of the compression pad 130 is of corrugated construction and has a fluid sealing film layer 140, such as of polyurethane, bonded thereto by a suitable adhesive, such as also polyurethane, with the resultant corrugations forming alternating ridges 142 and valleys 144. Preferably, as is best shown in FIGS. 6 and 7A, a second fluid sealing polyurethane film layer 146 also overlays the first sealing film layer 140 in corrugated form, with adjacent upper and lower edge portions 140e and 146e of the film layers adhesively bonded together at upper and lower bond joints 148 and 150, respectively, and with the intervening portions of the layers unbonded to enable subsequent removal of the second layer from the first layer, for replacement of the compression band-stay-pad assembly 32. The upper and lower edge portions 146e of the outer film layer 146 also are bonded to adjacent upper and lower edge portions 128e of the outer membrane 128 (which also may be formed of polyurethane), to form a fluid-tight enclosure. The resultant enclosure 128, 146, together with the drive mechanism housing 44, may be filled (such as through a suitable opening in the housing) with an inert lubricating medium 151, such as mineral oil, which also prevents body fluids from entering the ventricular assist device 20.

Referring to FIG. 6, the narrow portions 108n of the stay members 108, which have arcuate inner surfaces 108i, as shown in FIG. 7A, are disposed in respective ones of the valleys 144 formed by the corrugated pad assembly 126, for applying radially inward pressure on the pad assembly, and thus the heart 22, during its systole phase. Further, for more precise pressure control and to provide force transmission so as to further reduce the possibility of damage to the heart tissue or the pad assembly 126 by sharp edges or corners of the stays 108, as is best shown in FIG. 7A, a longitudinally and vertically extending coil spring 152 of circular cross-section and relatively small diameter, such as 0.16"±0.080", is disposed between each stay 108 and the outermost film layer 146 of the pad assembly 126, with the spring being adhesively bonded adjacent its center to the stay and along its length to the film layer.

Thus, as the stay 108 and the spring 152 move radially inward during a heart compression operation, in which the stay tends to move radially inward from a solid line position in FIG. 7A, the stay also tends to rotate slightly counterclockwise into a position as illustrated by broken lines in that figure as a result of the taper of the heart 22. Accordingly, the opposite end portions of the spring 152 tend to flex outwardly, from a slightly concave solid line position, to a convex position, as also shown by broken lines in FIG. 7A, with the pad assembly 126 adapting to this movement without damage to the pad assembly and/or the heart 22. Subsequently, when the stay 108 returns to its initial solid line position in FIG. 7A, during the diastole phase of the heart 22, the tendency of the spring 152 to return to its initial position facilitates restoration of the pad assembly 126, and thus the heart, to which it is secured, to their initial (diastole) conditions.

With further reference to FIGS. 4A and 5, the above-mentioned defibrillation electrodes 74 may be in the form of a plurality of small metallic cables 74c of numerous small diameter wires embedded in the foam pad 130 between the valleys 144 (FIG. 5) of the pad assembly 126, with lower ends of the cables being connected by lead wires of a small connector cable 153 (FIG. 4A) to the defibrillation pulse generator 72 (FIG. 1). The embedded cables 74c thus function effectively as large surface area defibrillating electrodes since the porosity of the foam pad 130 allows electric current to flow through to the heart 22 while the flexibility and strength of the small diameter wires of the cables effectively resist flex-fracturing.

As is best shown in FIG. 5, one end of the chain 38 is fixedly connected to the housing 44 of the energy converter and cardiac pumping mechanism 30, such as by a pin 153. The other end of the chain 38 is secured to the rotatable support spool 36, such as by a suitable lug-and-pin connection 154, so that the chain 38 can be wound thereon, or unwound therefrom. Opposite end ones of the stay links 111 also are pivotally connected to lug portions of the motor housing 44 by respective connector pins 155 and 156. Thus, during winding of the chain 38 upon the rotatable support spool 36, and unwinding of the chain therefrom, to cause alternate contraction and expansion of the compression band-stay-pad assembly 32, the chain or band moves longitudinally to cause radially inward and outward movement of the stays 108, springs 152 and the compression pad assembly 126, as previously described.

As is apparent from FIGS. 2, 3, 4A and 5, the band-stay-pad assembly 32, including the motor housing 44, encircles the heart 22 so as to be essentially independent of any other parts of the patient's body for support. Further, as is also shown in FIG. 6, the stays 108 are mounted on the chain 38 by the stay links 110 and 111, and are biased apart circumferentially by their associated return springs 114 so that the compression band-stay-pad assembly 32, including the motor housing 44, is constantly biased toward a radially outward position. When the chain 38 is wound on the support spool 36, however, the diameter of the assembly 32 (including the motor housing) encircling the heart 22, is reduced so that the stays 108 and the stay links 110 and 111 move toward one another circumferentially, compressing the springs 114, with the stays also moving radially inward about the perimeter of the heart to heart-compressing positions. Thus, during the systolic phase of the heart 22, substantially the entire perimeter of the heart (except for a small portion adjacent the motor housing 44) can be compressed essentially uniformly radially inward, and during the diastolic phase of the heart, the heart can expand in a similar manner radially outward. Further, during the latter movement, as a result of the foam pad 130 being secured to the heart 22 by suturing and/or ingrowth of the heart tissue, the springs 114, and also the springs 152, assist the heart in returning to its expanded condition.

FIGS. 7A, 7B and 7C illustrate an above-mentioned feature of the invention by which essentially the entire compression band-stay-pad assembly 32 may be replaced during surgery, leaving the inner foam pad 130, which has become ingrown with heart tissue, in situ on the heart. For this purpose, as is illustrated schematically in FIG. 7B, to remove the band-stay-pad assembly 32 while leaving the foam pad 130 in situ, a surgeon may cut the innermost film layer 140, which is bonded to the foam pad, from the outermost film layer 146 and thus the outer membrane 128 in a suitable manner. For example, the surgeon may cut the innermost film layer 140 from the outermost film layer 146 along cut lines 157 adjacent (but slightly spaced from) the bond joints 148 and 150 (FIG. 7A) for the layer edge portions 140e and 146e, whereupon the entire compression band-stay-pad assembly 32, except for the foam pad 130 and the innermost film layer 140 bonded thereto, can be removed from the heart 22. Referring to FIG. 7C, remaining opposite end portions 140er of the innermost film layer 140 then can be attached to opposite edge portions 146eR of a replacement compression band-stay-pad assembly (not shown), by suitable bonding and suturing, as illustrated schematically in this figure.

FIGS. 8A, B and C illustrate a second embodiment of the invention in which the motor-driven compression band-stay-pad assembly 32, including the circumferentially extending return springs 114, is replaced by a stay-pad assembly 32' comprising a plurality of motor or power assist devices 158 for respective sets of stays 108'. For example, one of the power assist devices 158 may be provided for each set of every five of the stays 108', as is shown in FIG. 8A.

Figure 8C:
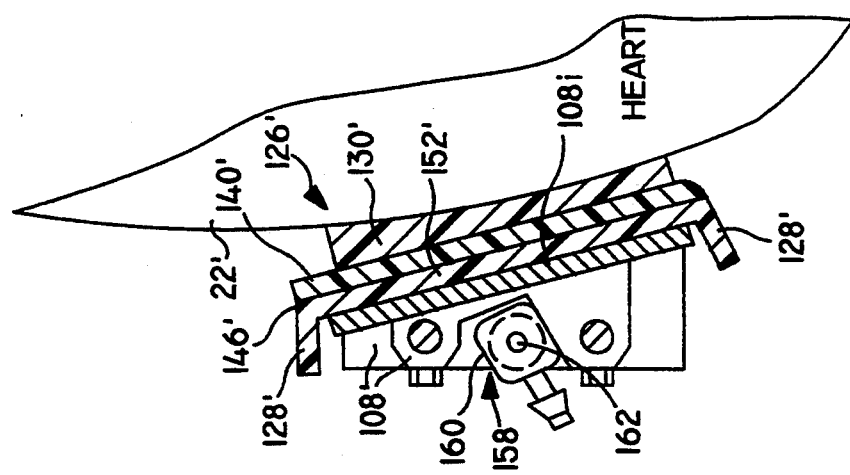
FIG. 8C is a cross-sectional view taken along the line 8C—8C in FIG. 8B.

For this purpose, every fifth or "corner" stay 108' is in the form of a tapered, wedge-shaped block member having facing sides of the stays parallel to one another. The next adjacent intermediate stays 108' have a modified C-shape, as is best shown in FIG. 8C, with relatively narrow inner portions and relatively wide outer portions, as is best shown in FIG. 8A. A central stay 108' also is of the modified C-shape, but of uniform width, as also best shown in FIG. 8A.

In this instance, each power assist device 158 is a double-acting hydraulic actuator or motor having a cylinder member 160 fixed, such as by welding, to one of the corner stays 108', and a piston rod 162 similarly secured by welding to the other corner stay of the set. Thus, by selective operation of the actuator 158, the corner stays 108' of the set can forcibly be pulled toward one another to assist in compression of a heart 22' in its systole phase, and forcibly moved apart during the heart's diastole phase.

Each set of the stays 108' also includes upper and lower guide pins 164 extending horizontally through apertures in upper and lower portions of the corner stays, intermediate stays and central stays, with the guide pins 164 fixed to the central stays by suitable welding 166, and slidably received in the intermediate stays and the corner stays of the set. Relative movement between the intermediate stays 108' and the corner stays 108' is limited by retaining members 168 having first ends secured (e.g., welded) to the corner stays and having lost motion slots 170 (FIG. 8B) at their opposite ends for receiving projecting pins 172 on the intermediate stays. In adjacent sets of the stays 108', as is best illustrated in FIG. 8B, similar guide pins 174 and retaining members 175 also are provided, but are located at different levels than the guide pins 164 and retaining members 172, to prevent interference therebetween.

As is shown in FIG. 8C, in this embodiment of the invention, each stay member 108' has an innermost inclined planar surface 108i', instead of a curved surface such as the curved surface 108i in the embodiment of the invention shown in FIGS. 1-7. Thus, a force transmitting small coil spring 152' is, in this instance, of relatively straight construction, and remains essentially so during heart systolic and compression phases, rather than moving between concave and convex positions, as in the case of the spring 152 of that embodiment. In other respects, the function of the spring 152', and an associated pressure pad assembly 126', including a foam pad 130' and edge-bonded sealing film layers 140' and 146', with the latter film layer also bonded to an outer membrane 128', is essentially the same as in the previous embodiment.

Figure 9:
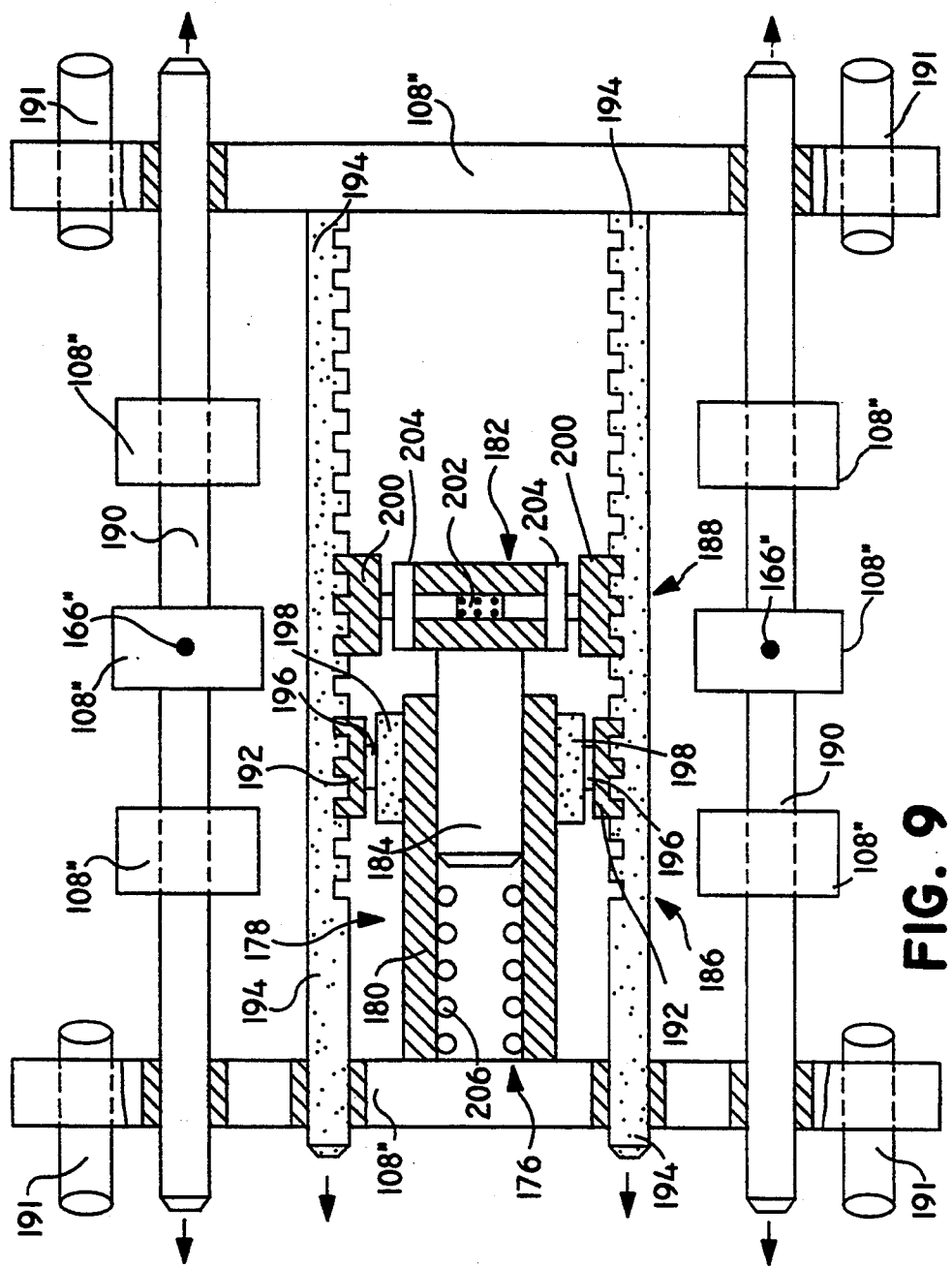
FIG. 9 is a partial elevational and cross-sectional view of a third embodiment of the invention.

FIG. 9 discloses a third embodiment of the invention similar to that disclosed in FIGS. 8A, B and C, in which each of a plurality of motor or power assist devices 176 (only one shown) includes a main solenoid 178 comprising a cylindrical coil assembly 180 fixedly mounted on one of two corner stays 108" and a T-shaped actuator mechanism 182, including an armature portion 184, slidably disposed in the cylindrical coil assembly. The coil assembly 180 also carries a first latching mechanism 186 and a projecting outer end of the actuator mechanism 182 includes a second latching mechanism 188. Upper and lower guide pins 190 also are fixedly mounted in central stays 108" by welding 166", and slidably mounted in both of the corner stays 108" and intermediate stays 108" as in the embodiment of the invention shown in FIGS. 8A, B and C, with guide pins 191 for adjacent sets of the stays similarly mounted at different levels.

The first latching mechanism 186 comprises vertically movable upper and lower latch members 192 slidably mounted for vertical movement on the coil assembly 180 and having respective upper and lower ends formed with teeth which are selectively engageable in notches of upper and lower bar racks 194, respectively. As viewed in FIG. 9, the bar racks 194 are fixed to the right-hand corner stay 108" and slidably received in the left-hand corner stay 108". The latch members 192 are movable into and out of engagement with the bar racks 194 by respective springs 196 and associated first small solenoids 198. The second latching mechanism 188 similarly comprises upper and lower latch members 200 which are biased to latching positions by a single return spring 202, and movable out of their latching positions by second small operating solenoids 204.

More specifically, at the beginning of a systole phase of a heart (not shown), with the stays 108" in their open positions, the first latch members 192 are disengaged from the racks 194 and the second latch members 200 are engaged therewith. The main solenoid 178 then is operated momentarily so that the second latch members 200 move the racks 194 and the right-hand corner stay 108" to the left (as viewed in FIG. 9) one increment, at which time the first small solenoids 198 are deenergized so that the springs 196 move the first latch members 192 into holding engagement with the racks, whereupon the second small solenoids 204 are energized to retract the second latch members 200. The main solenoid 178 then is deenergized so that a coil return spring 206 extends the second latching mechanism 188 for advancing the bar racks 194 another increment. Next, the second latch members 200 are released by their solenoids 204 so that their return spring 202 moves the latch members back into engagement with the racks 194, whereupon the first latch members 192 are retracted from rack engagement by their solenoids 198. The incrementing process then is repeated until a desired closure of the stays 108" has been achieved, with the process being repeated in reverse for a heart diastole phase.

Figure 10:
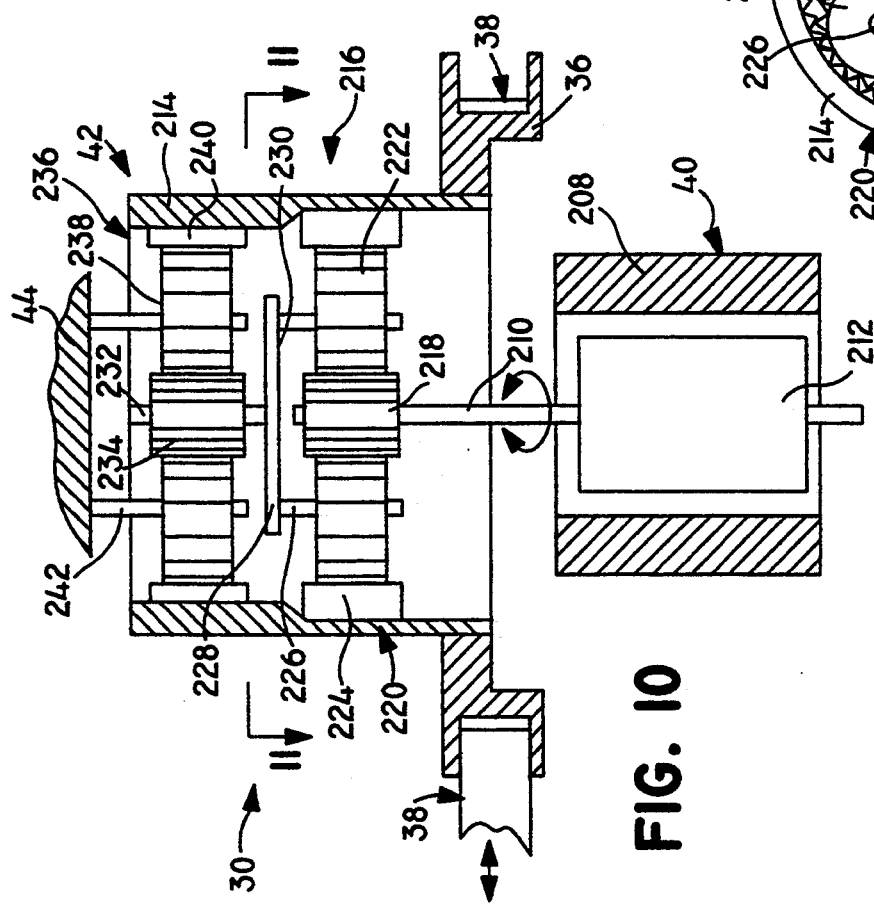
FIG. 10 is a schematic, elevational and cross-sectional view of a compression band operating mechanism of the ventricular assist device shown in FIGS. 1–7.

Referring again to the first embodiment of the invention and FIG. 10, the motor 40 of the energy converter and cardiac pumping mechanism 30 includes a fixed stator 208 and a drive shaft 210 extending from a rotor 212 coaxial with and partially located within a hollow cylindrical drive member 214 of the speed reducing mechanism 42. Further, an upper end of the motor drive shaft 210 is connected to the speed reducer drive member 214 via a planetary gear system 216. The rotatable support spool 36 is fixedly mounted on a lower portion of the speed reducer drive member 214 in a suitable manner, also not shown.

Figure 11:
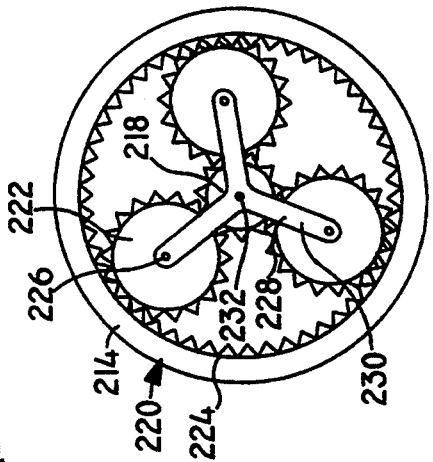
FIG. 11 is a cross-sectional view of the compression band operating mechanism taken essentially along the line 11—11 in FIG. 10.

Referring to FIGS. 10 and 11, an upper end of the drive motor shaft 210 includes a gear 218 which forms a sun gear of a lower planetary gear system 220, with the sun gear being drivingly engaged with three planetary gears 222 (see FIG. 11), in turn engaged with a ring gear 224 fixedly mounted to the interior of the hollow speed reducer drive member 214. The planetary gears 222 are mounted for rotation on vertical shafts 226 secured at their upper ends to respective arms 228 of a support member 230 having at its center a vertical shaft 232 upon which a second sun gear 234 of an upper planetary gear system 236 is fixedly mounted. As is shown in FIG. 10, the second sun gear 234 also is drivingly engaged with three planetary gears 238, in turn engaged with a second ring gear 240 fixedly mounted to the interior of the hollow speed reducer drive member 214. The second planetary gears 238 also are rotatably supported on depending shafts 242 mounted at their upper ends in a top wall of the housing 44. Thus, operation of the motor 40 in one direction causes winding of the compression band or chain 38 on the rotatable support spool 36 to wind the band thereon and cause inward radial movement of the compression band-stay-pad assembly 32 to assist the heart 22 in its systole phase, and operation of the motor in the reverse direction permits unwinding of the band from the rotatable support member to permit the abovementioned radially outward expansion of the compression band-stay-pad assembly during the diastole phase of the heart.

FIGS. 12A and B illustrate the construction of the end wrapping portion of the link chain 38 which is secured to the rotatable support spool 36 and wound upon the support spool to contract the compression band-stay-pad assembly 32 during a heart systolic phase, and then unwound from the support spool to permit the compression assembly to retract outward in a heart diastolic phase. In this connection, this portion of the chain 38 is of essentially the same construction as the compression portion of the chain previously described, comprising a series of chain link members 116 interconnected by pivot pins 118 fixed at upper and lower ends in the apertures 120 in the link member legs 116h, and having intermediate portions journaled in the wear-resistant cylindrical bearings 122 in the link member central portions 116c, except that the end link member is adapted to be connected to the rotatable support spool by the pin 154. Further, inner surface portions 116s of the chain members 116 which engage against the support spool 36 are formed with a curved radius, such as one inch, to facilitate the winding of the chain members on the support spool.

Figure 13A:
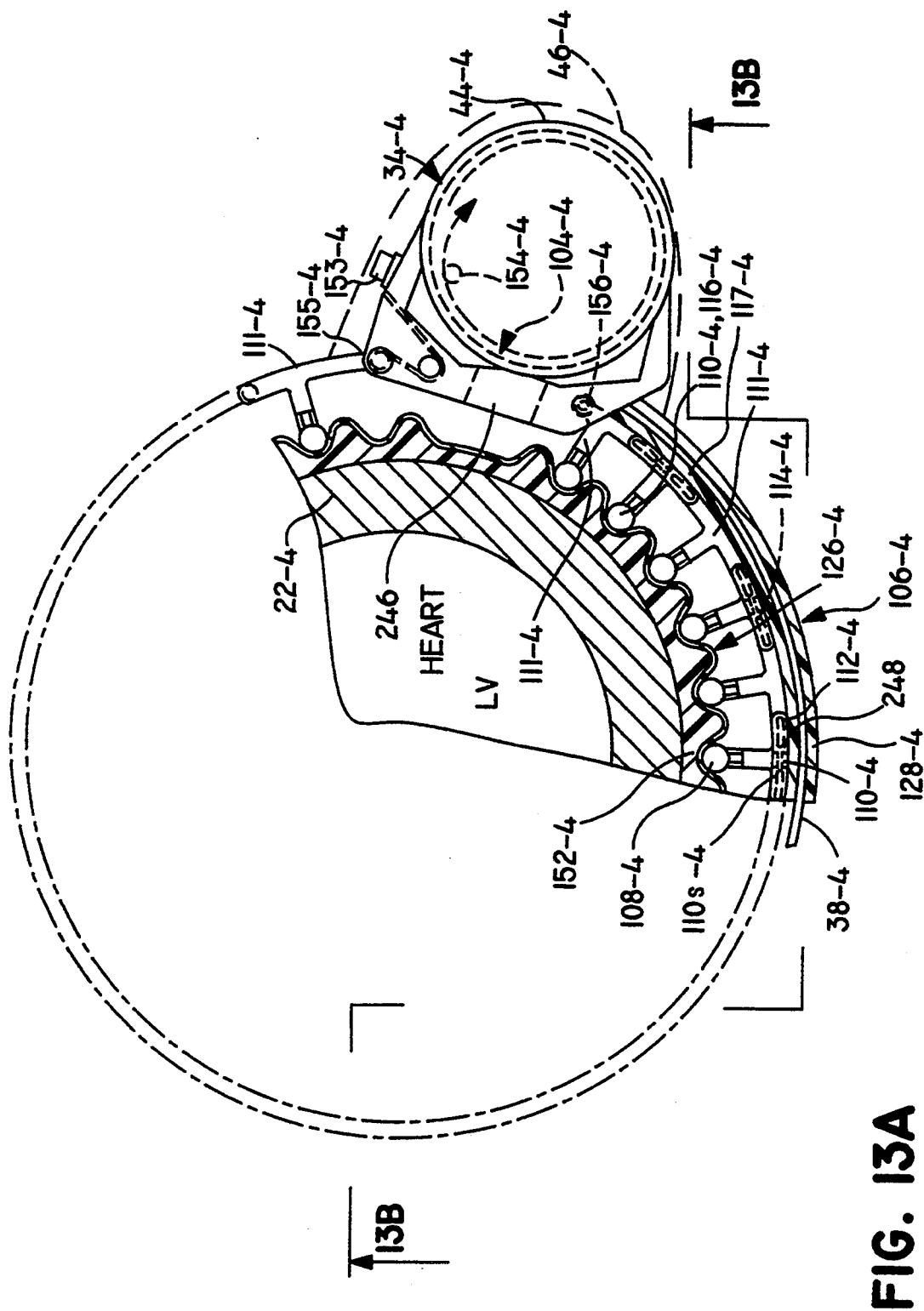
FIG. 13A is a schematic, partial cross-sectional view of a fourth embodiment of the invention, taken essentially along the line 13A—13A in FIG. 13B.
Figure 13B:
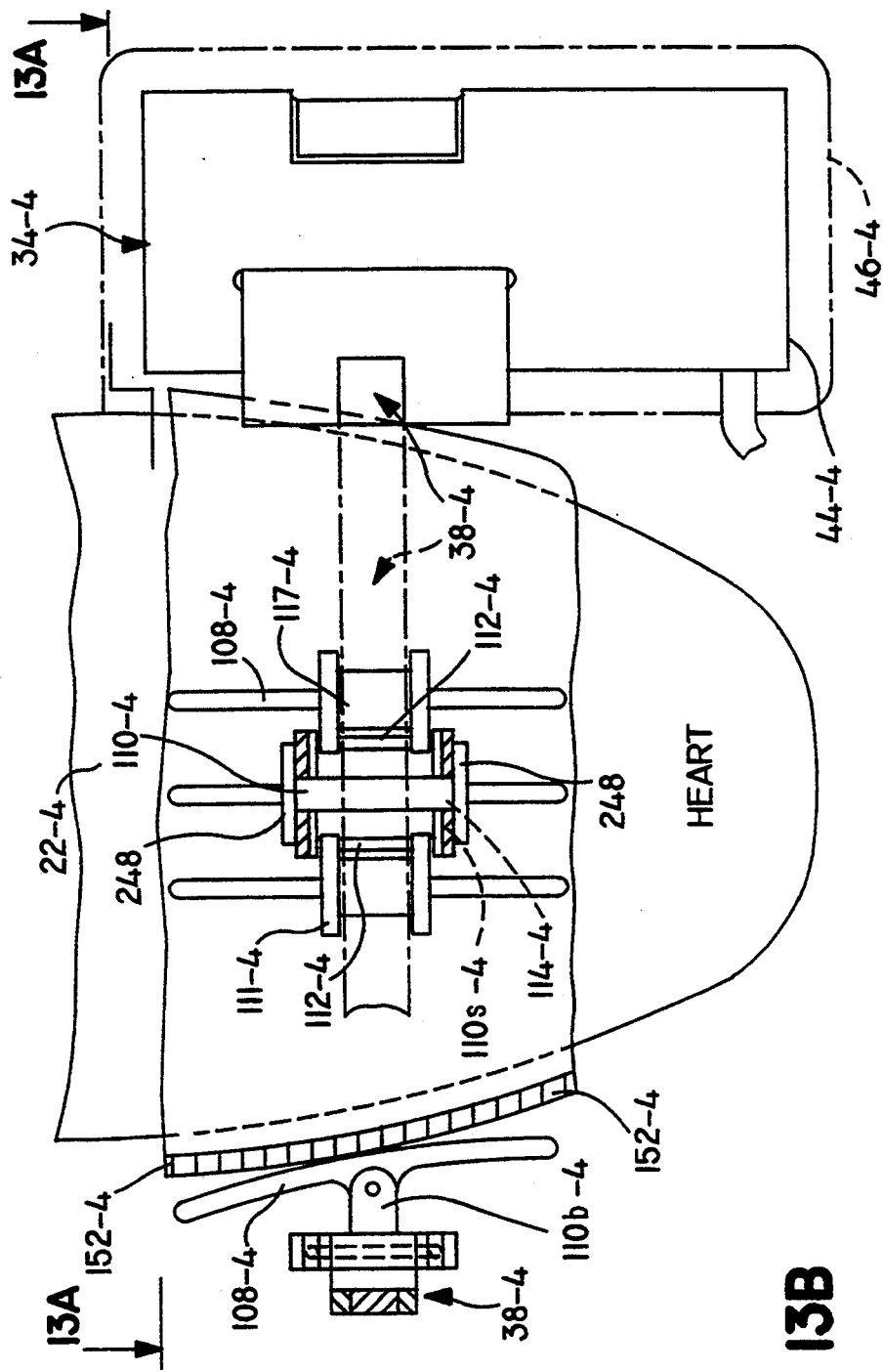
FIG. 13B is a schematic, partial cross-sectional view, with certain parts omitted, taken essentially along the line 13B—13B in FIG. 13A.

A fourth embodiment of the invention, as disclosed in FIGS. 13A and 13B, is of similar construction to the first embodiment of the invention, as disclosed in FIGS. 2–7C. In this connection, this embodiment includes a compression band-stay-pad assembly 32-4, comprising a series of arcuate stay members 108-4 mounted for pivoted rocking movement on alternating stay link members 110-4 and 111-4 by pivoted connections 110b-4 and 111b-4, with the stay members being provided with curved coil springs 152-4. An end one of the stay link members 111-4 is pivotally connected to a fixed member 246 on a housing 44-4 of a drive mechanism 34-4, by a connector pin 155-4, and an opposite end one of the stay link members is similarly connected to the fixed member 246 by a connector pin 156-4. A compression band, in the form of a chain 38-4, encircles the stay link members 110-4 and 111-4, with the chain being fixedly connected at one end on the fixed member 246 by a connector 153-4, and connected at its opposite end, by a connector 154-4, to a rotatable support spool 36-4 of the drive mechanism 34-4. The foregoing assembly is encased in a protective structure 106-4 filled with a lubricating medium and comprising a pad assembly 126-4 and an outer membrane 128-4, with the housing 44-4 also encased in a suitable biocompatible casing 46-4.

The embodiment of FIGS. 13A and 13B differs from the embodiment of FIGS. 2–7C in that the stay members 108-4 are of circular cross-section, rather than of a relatively complex configuration as disclosed in that embodiment. Further, rather than the compression band-stay-pad assembly 32-4 being circumferentially biased by the springs 114 between the stay members 108, this biasing is achieved by springs 114-4 disposed in slots 110s-4 in the stay link members 110-4, with the springs being located between end portions of hinge pins 112-4, for interconnecting these stay link members with the stay link members 111-4, and opposite ends of the slots. To retain the springs 114-4 in the slots 110s-4, the upper and lower legs 110h of the stay link members 110-4 are provided with cover members 248, secured thereon in a suitable manner, such as by welding or small screws (not shown). Further, since in this embodiment the stay link members 110-4 and 111-4 tend to close together to a greater degree during a heart contraction-assist operation, than the stay link members 110 and 111 in the embodiment of FIGS. 2–7C, if all of the stay link members were provided with the arcuate bearing surfaces 117, the surfaces would interfere with one another during a closing operation; accordingly, in this embodiment only the stay link members 111-4 are provided with arcuate bearing surfaces 117-4 for supporting the chain 38-4 during its movement relative to the stay link members, with the stay link members 110-4 being of a modified construction as shown. In other respects, the structure and operation of the embodiment of FIGS. 13A and 13B is essentially identical to the embodiment of the invention disclosed in FIGS. 2–7C.

Figure 14A:
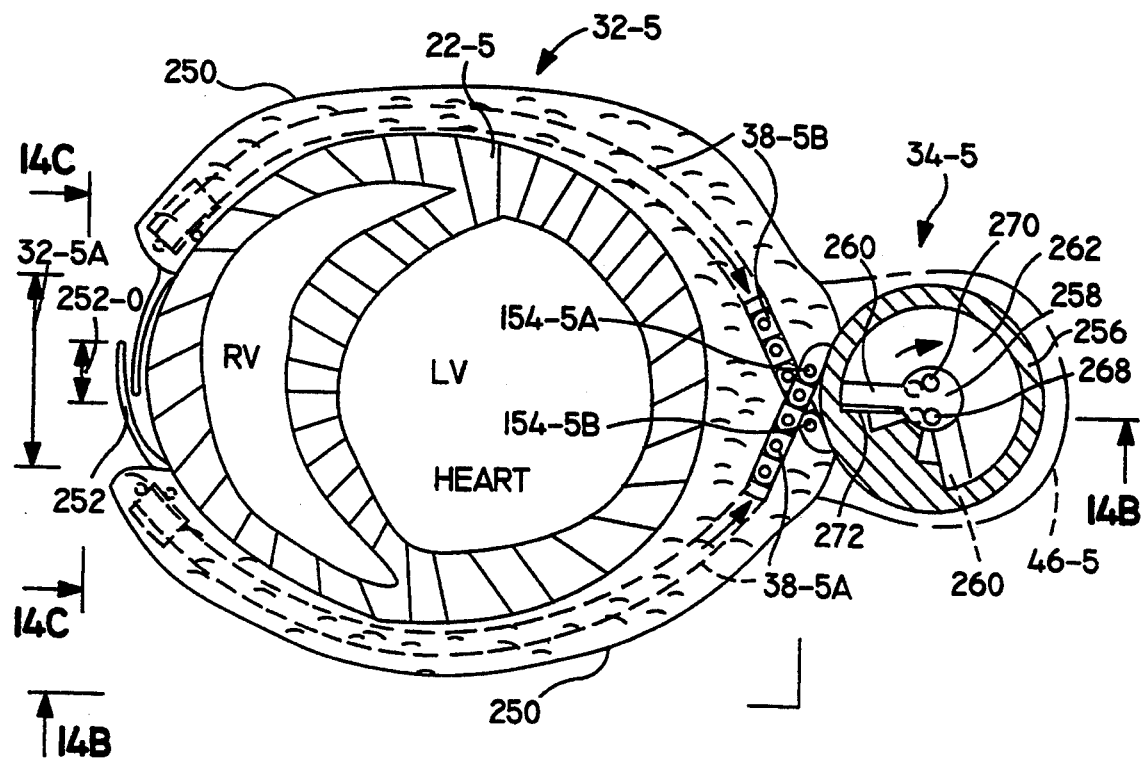
FIG. 14A is a schematic, partial cross-sectional view of a fifth embodiment of the invention, taken essentially along the line 14A—14A in FIG. 14B.
Figure 14B:
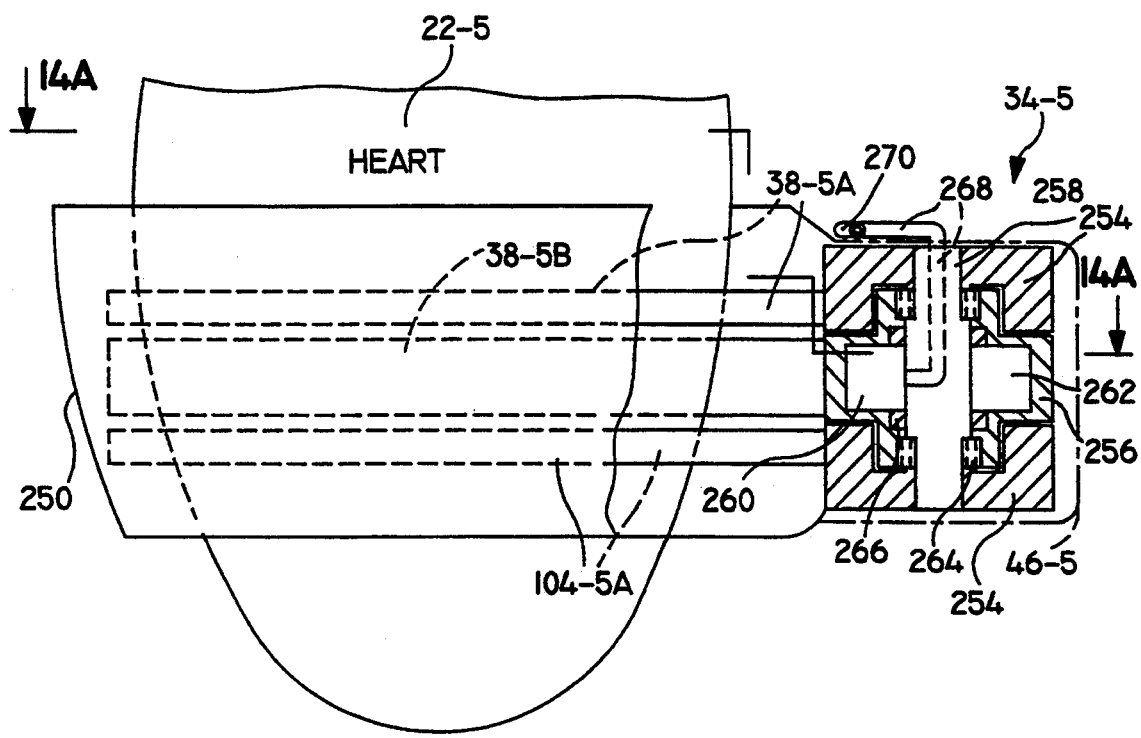
FIG. 14B is a schematic view, partially in cross-section, taken essentially along the line 14B—14B in FIG. 14A.

FIGS. 14A, B and C disclose a fifth embodiment of the invention in which a compression band-stay-pad assembly 32-5 is constructed in the form of two essentially arc-shaped portions 250 each connected to a drive mechanism 34-5 at one end (right-hand in FIGS. 14A and B) and initially unconnected at an opposite end (left-hand in FIGS. 14A and B) and separated so as to provide an adjustable portion 32-5A, so that the compression band-stay-pad assembly can be adjusted to size as it is fitted to a patient's heart 22-5, and thus "customized" depending upon size of the heart. Further, in this embodiment, rather than being moved into a heart contracting-assist condition (systole) by a single chain secured at one end and wound up at its opposite end, the compression band-stay-pad assembly 32-5 is contracted by multiple chains being wound up in opposite directions simultaneously.

Figure 3:
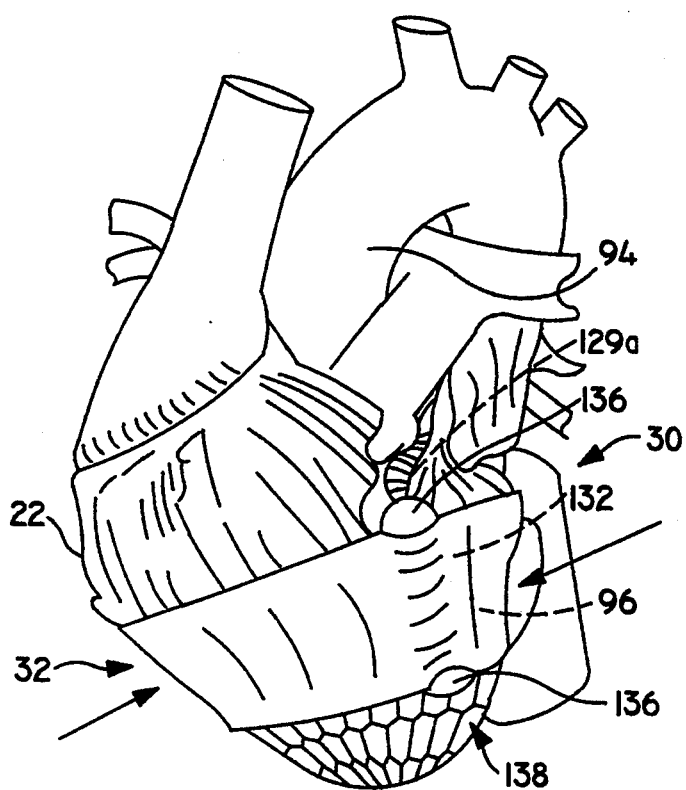
FIG. 3 is a schematic view showing the patient's heart and the ventricular assist device during a systolic phase of the heart.
Figure 14C:
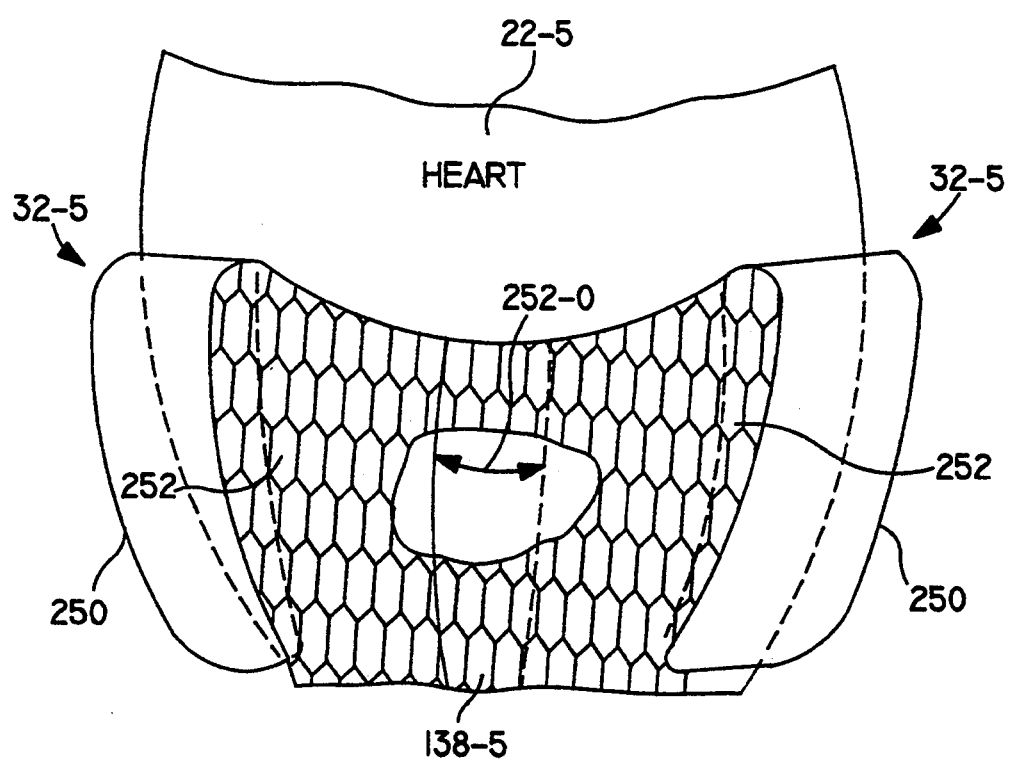
FIG. 14C is a schematic elevational view as seen essentially along the line 14C—14C in FIG. 14A.

For this purpose, as is best shown in FIG. 14C, a net structure 138-5 for supporting an apical portion of the heart 22-5 is provided on the compression band-stay-pad assembly 32-5, as disclosed in the first embodiment of the invention in FIGS. 3 and 4A, with parts 252 of the net being extended upward between the adjacent initially unconnected ends of the compression band-stay-pad assembly, suitably secured to the adjacent initially unconnected ends, and having partially overlapping portions 252-0. The parts 252 of the net 32-5 then may be used by a surgeon to pull the compression band-stay-pad assembly 32-5 into tight-fitting relationship with respect to the heart 22-5 when it is in its diastolic phase, whereupon the overlapped portions 252-0 may be suitably secured together. Thus, the compression band-stay-pad assembly 32-5 can be "custom-fit" to the heart 22-5, as noted previously.

Further, to contract the thus "customized" compression band-stay-pad assembly 32-5 about the heart 22-5 in its systolic phase, a pair of upper and lower chains 38-5A and an intermediate chain 38-5B movable therebetween adjacent a drive mechanism 34-5, are provided. In this instance, the drive mechanism 34-5 is of a hydraulic type and comprises upper and lower housing members 254 and an intermediate housing member 256 capable of free rotation in a casing 46-5 which is filled with lubricant as a result of being in fluid communication with the adjacent ends of the compression band-stay-pad assembly 32-5. A vertical shaft 258 extends downwardly through the housing members 254 and 256, with the upper and lower housings 254 being fixedly mounted to upper and lower end portions of the shaft, respectively. Fixed to an intermediate portion of the shaft 258 is a vane member 260 which is movable in an arcuate inner chamber 262 within the intermediate housing 256, with the intermediate housing being rotatably mounted on the shaft by suitable bearings 264, and with the arcuate inner chamber 262 being of liquid-tight construction as a result of suitable seals 266 encircling the shaft at upper and lower ends of the chamber.

A liquid inlet line 268 and a liquid outlet line 270 also are suitably connected to the upper end of the shaft 258, with the inlet line feeding vertically downward through the shaft and opening into the inner chamber 262 of the intermediate housing 256 between the vane 260 and an adjacent chamber wall 272. Similarly, the outlet line 270 extends downward through the shaft 258 and opens into the inner chamber 262 on an opposite side of the vane 260. The upper and lower chains 38-5A are secured to respective ones of the upper and lower housings 254 by connectors 154-5A (one shown in FIG. 14A for the upper chain), and the intermediate chain 38-5B is similarly secured by a connector 154-5B (FIG. 14A) to the intermediate housing 256. The inlet and outlet lines 268 and 270 also are connected to a liquid source, comprising a pump and a storage chamber, not shown.

Thus, in operation, when liquid is introduced through the inlet line 268 into the inner chamber 262 of the intermediate housing 256 between the vane 260 and the adjacent inner wall 272, opposing thrust forces are created on the vane and the inner wall causing the vane and the shaft 258 to which it is secured, to rotate clockwise as viewed in FIG. 14A, while at the same time the intermediate housing is caused to rotate in an opposite direction counterclockwise in this figure. Further, since the upper and lower housings 254 are fixed to the vertical shaft 258, these housings also tend to rotate clockwise in FIG. 14A. Thus, the upper and lower chains 38-5A are wrapped upon their respective upper and lower housings 254 in a clockwise direction, while the intermediate chain 38-5B is wrapped upon the intermediate housing 256 in a counterclockwise direction, to cause contraction of the band-stay-pad assembly 32-5 about the heart 22-5 during its systolic phase.

Figure 15:
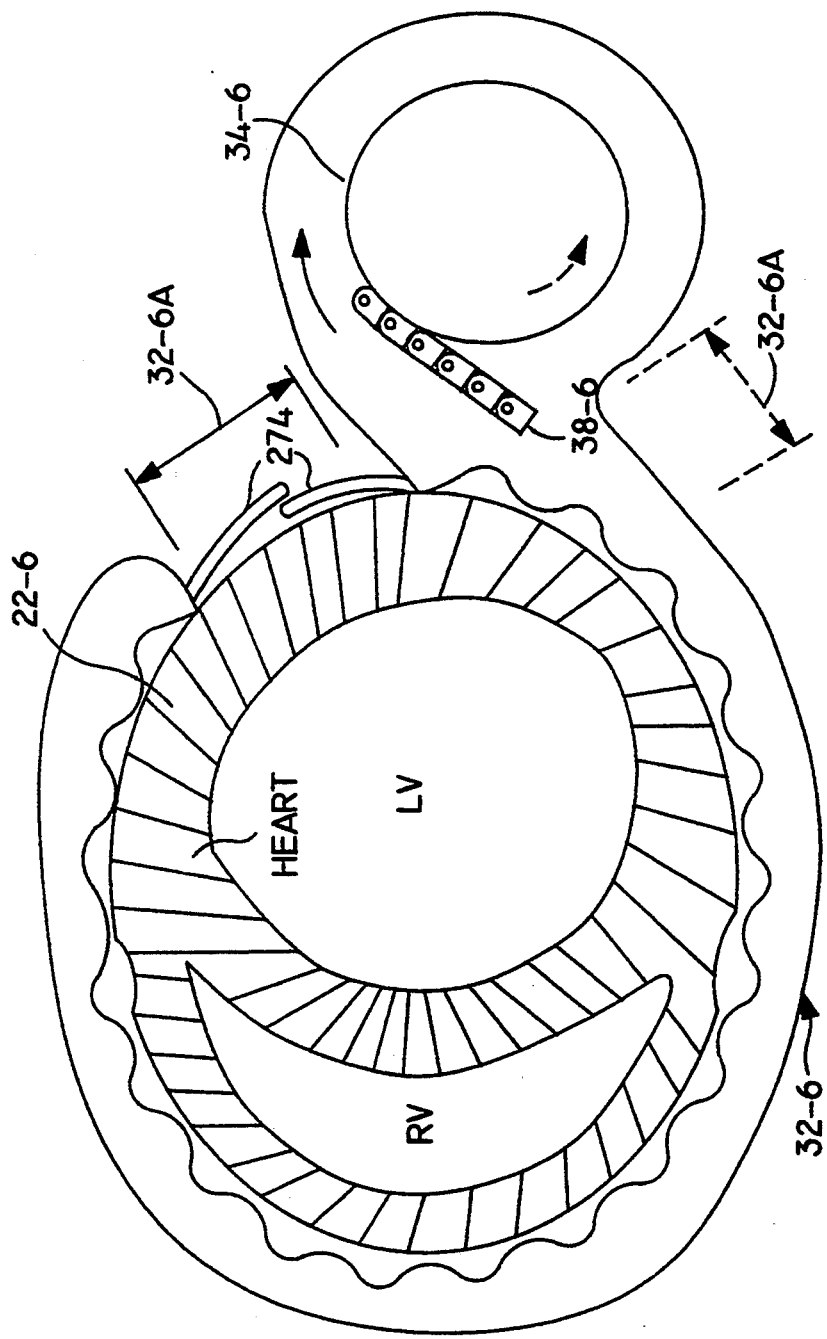
FIG. 15 is a schematic cross-sectional view illustrating a sixth embodiment of the invention.

FIG. 15 discloses a sixth embodiment of the invention, which, like the embodiment of the invention shown in FIGS. 14A, B and C, can be "custom-fit" to a patient's heart 22-6. In this instance, however, a compression band-stay-pad assembly 32-6 extends essentially around the entire periphery of the heart 22-6, with an adjustable portion 32-6A of the assembly being provided between a drive mechanism 34-6 at one end of the assembly, and an opposite end thereof. Thus, in this embodiment, as in the embodiment of the invention of FIGS. 14A, B and C, the "custom-fitting" of the compression band-stay-pad assembly 32-6 to the heart 22-6 can be accomplished by utilizing upwardly extending portions 274 of a net structure (not shown) for supporting an apical portion of the heart as disclosed in those figures. In this embodiment, however, only a single chain 38-6 is provided with the chain being wound up by the drive mechanism 34-6 in a clockwise direction, as indicated by the solid-line arrow in this figure. In the alternative, an adjustable portion 32-6A of the compression band-stay-pad assembly 32-6 may be provided adjacent the opposite side of the drive mechanism 34-6, as illustrated by broken lines, with the aforementioned chain then being wound up in a counter clockwise direction, as indicated by the broken line arrow in this figure.

In general, referring again to FIG. 1, in operation, the energy converter and cardiac pumping mechanism 30 converts electrical power signals, received from the electronic control system 50, to direct mechanical cardiac assist by the compression band-stay-pad assembly 32. Typically, data and power are transcutaneously transferred from the external controller 86 and battery pack 88 to the implanted electronic control system 50. The external battery pack 88 also can be selectively recharged by the battery charger 91, and periodic system programming can be accomplished by temporarily connecting the external controller 86 to the programmer 92. The internal batteries 56, contained in the electronic control system 50, provide system power for periods when the belt 100 (FIG. 2) containing the external controller/battery pack 86, 88 is temporarily removed by the patient user. In the alternative, the power line-operated stationary power supply 90 may be used in place of the patient-worn battery pack 88.

With further reference to FIG. 1, the electronic control system 50 regulates fundamental cardiac assist, pacer and cardioverter/defibrillation functions. In the normal operating mode, the electronic control system 50 monitors the electrocardiogram (ECG) signal received by the detector 66 from the ECG/pacer lead 70. Upon the detector circuit 66 detecting a ventricular contraction initiation (R-wave or QRS complex), a programmable delay period is initiated after which the motor 40 is driven forward causing the compression band-stay-pad assembly 32 to compress the myocardium of the heart 22. When the systolic cycle is complete, the motor 40 is returned to its end diastolic position, causing and/or permitting the compression band-stay-pad assembly 32 to expand radially outward.

In a pre-systolic phase, approximately 30 milliseconds before the next anticipated QRS complex (predicted by analyzing previous R to R intervals) a light preload pressure (programmable) is applied to the heart 22. This pressure minimizes mechanical shock loading and myocardial impact during the initial phase of the impending systolic assist cycle. At the same time, the electronic control system 50 also controls the pacer 68 and the defibrillator pulse generator 72.

With further reference to the pre-systolic phase, approximately 30 milliseconds prior to the next anticipated systolic cycle, the motor 40 is driven forward a programmed fixed amount. The arrival time of systole is predicted by storing the four most recent cycle periods with the shortest of the four periods being used to predict the onset of the impending cycle. If the current end diastolic position was set correctly, the compression band-stay-pad assembly 32 then should begin compressing the myocardium during the second half of the pre-systolic motor travel. A corresponding increase in the drive current of the motor 40 then will be required to finish the motor's travel in the pre-systolic phase and motor current may be monitored by the PWM motor drive circuit 80. However, if an increase in current is not observed by the controller 54, the end diastolic position of the compression band-stay-pad assembly 32 then will subsequently be modified (increased) to provide a "tighter" (more radially inward) end diastolic position, in preparation for the next systolic phase. Similarly, if a high motor drive current is observed by the controller 54 throughout the pre-systolic travel period of the motor 40, the end diastolic position will subsequently be modified (decreased) to provide a "looser" (more radially outward) end diastolic position of the compression band-stay-pad assembly 32. As an alternative, or in addition to monitoring motor current, the preload force interface 76 and the force transducer 77 may be used to directly measure the cardiac force exerted by the compression band-stay-pad assembly 32, and modify the end diastolic position accordingly. Other force-indicative parameters also may be measured and used for this purpose.

Typically, while as previously discussed, the systolic assist phase shown in FIG. 3 is triggered when a QRS complex is detected, an assist escape interval, such as 833 milliseconds, may also be programmed and enabled. The assist escape interval triggers the systolic assist phase (and a pacer pulse is output if the pacer 68 is enabled) if a QRS signal is not detected within a preselected time interval, or if there is continuous sensing of noise during the interval such that the QRS signal cannot be detected, thus effectively providing asynchronous assist if QRS sensing is lost. Alternately, the electronic control system 50 may be programmed to operate asynchronously at a selected rate (possibly used during ventricular fibrillation). Again, once the systolic phase is triggered, the programmable delay period is initiated, as previously described. When the delay period is complete, the motor 40 then is driven forward causing the compression band-stay-pad assembly 32 to compress the myocardium of the heart 22.

In summary, a new and improved biocompatible ventricular assist and arrhythmia control device 20 has been disclosed. For example, essentially the entire device 20 can be completely and readily implanted in the body of a patient user, and can operate independently of an external source from the battery pack 88 in the belt 100 being worn around the patient user's waist. The energy converter and cardiac pumping mechanism 30, including the compression band-stay-pad assembly 32, which can be secured directly to the patient user's heart 22, also provides a system which helps ensure positive compression and expansion assistance to the heart during its systolic and diastolic phases, respectively. During the systolic phase, the heart-engaging foam pad 130, film layers 140 and 146 and the force-transmitting vertical springs 152 cooperate to prevent damage to the heart. Further, the heart-engaging foam pad 130, the stay members 108, the circumferentially extending return springs 114 and the force-transmitting vertical springs 152, cooperate to facilitate the heart's expansion during the diastolic phase. As is illustrated in FIGS. 7A, B and C, the provision of the inner and outer film layers 140 and 146 on the foam pad 130 also enables removal of the compression band-stay-pad assembly 32, except for the inner film layer 140 and the foam pad 130 to which it is bonded, which remain in situ on the heart 22, and then replacing the removed assembly structure with a new compression band-stay-pad assembly structure. Further, in the invention embodiments of FIGS. 8A, B and C, and FIG. 9, respectively, the hydraulic actuator 30 mechanism 158 and the solenoid-latch mechanism 176 provide alternative modes of producing heart contraction and expansion assistance, while the embodiments of FIGS. 13A–15 provide other advantageous features.

It is to be understood that the foregoing description and accompanying drawings set forth the preferred embodiments of the invention at the present time. Various modifications, additions and alternative designs will, of course, become apparent to those skilled in the art in light of the foregoing teachings without departing from the spirit and scope of the disclosed invention. Therefore, it should be appreciated that the invention is not limited to the disclosed embodiments but may be practiced within the full scope of the appendant claims.

We claim:

1. A ventricular direct mechanical assist device, which comprises:
   a series of force-transmitting linked members for arrangement around a perimeter of a portion of a heart; and
   means for actuating said members to apply compression to the heart;
   wherein said members receive mechanical energy acting on said members and transmit mechanical energy to the heart.

2. The device as recited in claim 1, further comprising:
   means for moving said force-transmitting linked members in radial directions; and
   compression return springs interconnecting said force-transmitting linked members.

3. The device as recited in claim 2, which further comprises means for maintaining said compression return springs aligned with each other.

4. The device as recited in claim 1, further comprising a circumferentially movable band mechanism;
   wherein said force-transmitting linked members receive mechanical energy from said band mechanism through circumferential movement about the perimeter of the heart, thereby exerting force perpendicular to said heart perimeter.

5. The device as recited in claim 1, wherein at least a portion of said force-transmitting members are interconnected by a power mechanism for exerting at least a closure force perpendicular to and between said interconnected members.

6. The device as recited in claim 5, wherein said power mechanism includes a hydraulic cylinder and piston.

7. The device as recited in claim 5, wherein said power mechanism is a solenoid actuator.

8. The device as recited in claim 7, which further comprises latching means for capturing stroke motions produced by said solenoid actuator.

9. The device as recited in claim 1, which further comprises a resilient pad assembly having an outermost corrugated surface defining alternating ridges and valleys, and wherein each force-transmitting member further includes a longitudinally extending spring that supports said pad assembly and is received in a respective one of the valleys in the corrugated surface of said pad assembly.

10. The device as recited in claim 9, comprising means for flexing said pad assembly-supporting spring progressively towards opposite ends thereof during a force-transmitting operation, from a diastolic concave form to a systolic convex form.

11. A ventricular assist device which can be implanted in a patient user exterior to the heart adjacent at least one ventricle, and which comprises:
   compression band means for surrounding the perimeter of the heart and having a preselected perimeter length when the heart is in a diastolic phase;
   means for shortening the perimeter length when the heart is in a systolic phase; and
   force-transmitting means for receiving mechanical energy from said band means as its perimeter length is shortened and transmitting said energy to compress the heart in its diastolic phase.

12. A ventricular assist device which can be implanted in a patient user, which comprises:
   means for actively compressing the patient's heart; and
   a collapsible netting structure supporting an apical portion of the heart and connected to said compressing means.

13. The device as recited in claim 12, wherein the collapsible netting structure is a net capable of passive surface area contraction yet incapable of stretching beyond a preselected limit.

14. The device as recited in claim 13, wherein said net is formed from a fiber bundle having a diameter in a range on the order of 0.6 to 2.6 mm in diameter, and has openings having dimensions of approximately 3 by 8 mm.

15. The device as recited in claim 14, wherein said fiber bundle is constructed of polyester.

16. A ventricular assist device which can be implanted in a patient user, which comprises:
   a contact surface for contacting the heart;
   means for contracting and expanding the contact surface of the assist device; and
   an electrically-driven motor attached to said means for contracting and expanding for causing contraction and expansion of said contact surface, said motor further including means for fitting in a natural cleavage plane between the left lung and diaphragm or the left lung and an inside chest wall of the patient.

17. A ventricular assist device which can be implanted in a patient user exterior to the heart, comprising:
elongated band means positionable around the entire perimeter of the heart;
rotatable support means for winding at least a portion of the band means thereon and unwinding the portion of the band means therefrom, the band means being connected to the rotatable support means;
resilient pad means for engaging the heart and applying pressure thereto in response to movement of said band means;
means for sensing the systolic and diastolic phases of the heart; and
reversible drive means for rotating the rotatable support means in one direction to wind the portion of the band means thereon and thereby compressing the heart ventricle during a systolic phase thereof, and for rotating the rotatable support means in a reverse direction to unwind the portion of the band means from the rotatable support means, to release the heart during a diastolic phase thereof.

18. The ventricular assist device as recited in claim 17, wherein the drive means includes a drive motor and a speed reducer connected to the rotatable support means.

19. The ventricular assist device as recited in claim 18, wherein the speed reducer includes at least one planetary gear system connected between the drive motor and the rotatable support means.

20. The ventricular assist device as recited in claim 19, wherein the planetary gear system includes a sun gear mounted on a drive shaft of the drive means.

21. The ventricular assist device as recited in claim 17, wherein the resilient pad means is at least partially of corrugated construction.

22. The ventricular assist device as recited in claim 17, which further comprises protective means for encasing the band means, the protective means including the resilient pad means.

23. The ventricular assist device as recited in claim 22, which further comprises lubricating medium contained in the protective means.

24. The ventricular assist device as recited in claim 23, wherein the resilient pad means includes a porous member having a heart-engaging surface on an inner side thereof and a sealing film on an outer side thereof.

25. The ventricular assist device as recited in claim 24, which further comprises:
a second sealing film having opposite edge portions secured to respective opposite edge portions of said first-mentioned film, with intermediate portions of said films being unsecured to one another; and
a sealing membrane forming part of said protective structure and having opposite edge portions also secured to said edge portions of said sealing films and cooperating with said films to encase said band means.

26. The ventricular assist device as recited in claim 25, wherein the resilient pad means includes spring means for returning the resilient pad means from an end systolic condition to an end diastolic condition.

27. The ventricular assist device as recited in claim 26, wherein said spring means are elongated coil springs bonded to said resilient pad means.

28. The ventricular assist device as recited in claim 17, wherein the resilient pad means includes spring means for returning the resilient pad means from an end systolic condition to an end diastolic condition.

29. The ventricular assist device as recited in claim 17, which further comprises means for slidably supporting said band means, said support means being formed of plastic when said band means is formed of metal, and being formed of metal when said band means is formed of plastic.

30. The ventricular assist device as recited in claim 17, wherein the band means is a chain.

31. The ventricular assist device as recited in claim 17, which further comprises:
force-transmitting members disposed between said band means and said resilient pad means.

32. The ventricular assist device as recited in claim 31, which further comprises compression return springs disposed between respective ones of said force-transmitting members.

33. The ventricular assist device as recited in claim 31, wherein said force-transmitting members are each comprised of a plurality of support members, at least some of which have surface means for supporting said band means for movement relative to said support members.

34. The ventricular assist device as recited in claim 33, further comprising pin-and-slot connections, wherein said support members are interconnected by said pin-and-slot connections so as to be contractible and expandable circumferentially.

35. The ventricular assist device as recited in claim 34, wherein said compression return springs are disposed in said pin-and-slot connections.

36. The ventricular assist device as recited in claim 17, wherein the band means includes biasing means for biasing the band means outward in the diastolic phase of the heart ventricle.

37. The ventricular assist device as recited in claim 36, which further comprises means for securing the band means to the heart ventricle.

38. The ventricular assist device as recited in claim 17, wherein the resilient pad means is formed, at least in part, of a soft porous foam material for engaging the heart.

39. The ventricular assist device as recited in claim 17, which further comprises:
external control means for controlling the reversible drive means transcutaneously;
an external battery pack connected to said control means; and
a belt adapted to be worn externally by the patient user, said belt housing said control means and said battery pack.

40. The ventricular assist device as recited in claim 39, which further comprises a contractible net means secured to said band means for supporting the apical portion of the heart, said band length adjustment means comprising portions of said net means extending between opposed portions of said band means and being adapted to be secured together in overlapped relationship.

41. The ventricular assist device as recited in claim 17, which further comprises means for adjusting the length of said band means.

42. The ventricular assist device as recited in claim 17, which further comprises means for immovably fixing one end of said elongated band means, with an opposite end of said band means being connected to said reversible drive means.

43. The ventricular assist device as recited in claim 17, wherein:

said elongated band means includes first compression band means positionable about a portion of the heart for heart-contracting movement in a first direction;

said elongated band means further includes second compression band means positionable about another portion of the heart for heart-contracting movement in a second direction; and said reversible drive means includes first and second reversible drive means for moving said first and second compression band means in their respective directions.

44. The ventricular assist device as recited in claim 43, wherein one of said compression band means comprises a pair of spaced band members and the other of said compression band means comprises a single band member movable between said spaced band members adjacent said reversible drive means.

45. The ventricular assist device as recited in claim 43, which further comprises means for adjusting the combined circumferential length of said first and second compression band means.

46. A ventricular assist device for direct mechanical assistance to a heart, which comprises:

means for sensing systolic and diastolic phases of the heart;

means for encircling and contracting the perimeter of a surface portion of the heart when the heart is in a diastolic phase; and resilient means for cyclically shortening and lengthening said encircling means in a perimeter direction during systolic and diastolic phases of the heart, respectively, and for receiving and transmitting mechanical compression force to the surface portion of the heart.

* * * * *